(12) United States Patent  
Troxler

(10) Patent No.: US 8,011,248 B2  
(45) Date of Patent: Sep. 6, 2011

(54) METHODS, SYSTEMS, AND COMPUTER PROGRAM PRODUCTS FOR DETERMINING A PROPERTY OF CONSTRUCTION MATERIAL

(75) Inventor: Robert Ernest Troxler, Raleigh, NC (US)

(73) Assignee: Troxler Electronic Laboratories, Inc., Research Triangle Park, NC (US)

(*) Notice: Subject to any disclaimer, the term of this patent is extended or adjusted under 35 U.S.C. 154(b) by 0 days.

(21) Appl. No.: 12/551,241

(22) Filed: Aug. 31, 2009

(65) Prior Publication Data

US 2009/0314090 A1  Dec. 24, 2009

Related U.S. Application Data

(62) Division of application No. 11/513,334, filed on Aug. 30, 2006, now Pat. No. 7,581,446.

(60) Provisional application No. 60/712,754, filed on Aug. 30, 2005, provisional application No. 60/719,071, filed on Sep. 21, 2005.

(51) Int. Cl.  
*G01M 7/00* (2006.01)  
*G01N 29/00* (2006.01)

(52) U.S. Cl. .......................... 73/588; 73/594

(58) Field of Classification Search .............. 73/582, 73/588, 594; 324/663, 654, 691, 689; 702/182, 702/189, 127  
See application file for complete search history.

(56) References Cited

U.S. PATENT DOCUMENTS

| | | |
|---|---|---|
| 3,544,793 A | 12/1970 | Bless et al. |
| 3,635,082 A | 1/1972 | Prellwitz et al. |
| 3,794,843 A | 2/1974 | Chen |
| 4,219,776 A | 8/1980 | Arulanandan |
| 4,442,701 A | 4/1984 | Cowherd et al. |
| 4,525,854 A | 6/1985 | Molbert et al. |
| 4,641,030 A | 2/1987 | Regimand |
| 4,701,868 A | 10/1987 | Regimand |
| 4,766,319 A | 8/1988 | Regimand |

(Continued)

FOREIGN PATENT DOCUMENTS

GB     863886     3/1961

(Continued)

OTHER PUBLICATIONS

Official Action for Chinese Patent Application No. 200680040215.X (Apr. 29, 2010).

(Continued)

*Primary Examiner* — Helen C. Kwok  
(74) *Attorney, Agent, or Firm* — Jenkins, Wilson, Taylor & Hunt, P.A.

(57) ABSTRACT

Methods, systems, and computer program products for determining a property of construction material. According to one aspect, a material property gauge operable to determine a property of construction material is disclosed. The gauge may include an electromagnetic sensor operable to measure a response of construction material to an electromagnetic field. Further, the electromagnetic sensor may be operable to produce a signal representing the measured response by the construction material to the electromagnetic field. An acoustic detector may be operable to detect a response of the construction material to the acoustical energy. Further, the acoustic detector may be operable to produce a signal representing the detected response by the construction material to the acoustical energy. A material property calculation function may be configured to calculate a property value associated with the construction material based upon the signals produced by the electromagnetic sensor and the acoustic detector.

26 Claims, 24 Drawing Sheets

U.S. PATENT DOCUMENTS

| | | | |
|---|---|---|---|
| 4,904,942 A | | 2/1990 | Thompson |
| 5,095,465 A | | 3/1992 | Stokoe, II |
| 5,333,502 A | | 8/1994 | Clark, Jr. et al. |
| 5,457,628 A | | 10/1995 | Theyanayagam |
| H1561 H | | 7/1996 | Thompson |
| 5,614,670 A | | 3/1997 | Nazarian et al. |
| 5,900,736 A | * | 5/1999 | Sovik et al. ........... 324/663 |
| 6,272,434 B1 | | 8/2001 | Wisler et al. |
| 6,310,936 B1 | | 10/2001 | Troxler et al. |
| 6,369,381 B1 | | 4/2002 | Troxler et al. |
| 6,393,921 B1 | | 5/2002 | Grimes et al. |
| 6,397,661 B1 | | 6/2002 | Grimes et al. |
| 6,400,161 B1 | | 6/2002 | Geisel |
| 6,411,087 B1 | | 6/2002 | Fan et al. |
| 6,414,497 B1 | * | 7/2002 | Sovik et al. ........... 324/663 |
| 6,427,774 B2 | | 8/2002 | Thomas et al. |
| 6,442,232 B2 | | 8/2002 | Troxler et al. |
| 6,604,432 B1 | | 8/2003 | Hamblen et al. |
| 6,677,763 B2 | | 1/2004 | Geisel |
| 6,803,771 B2 | | 10/2004 | Sovik et al. |
| 6,823,736 B1 | | 11/2004 | Brock et al. |
| RE38,910 E | | 12/2005 | Troxler et al. |
| 7,040,145 B2 | | 5/2006 | Drnevich et al. |
| 7,042,801 B1 | | 5/2006 | Berg |
| 7,107,159 B2 | | 9/2006 | German |
| 7,219,024 B2 | * | 5/2007 | Gamache et al. ........... 702/65 |
| 7,376,530 B2 | * | 5/2008 | Bienvenu et al. ........... 702/127 |
| 7,569,810 B1 | | 8/2009 | Troxler et al. |
| 7,581,446 B2 | | 9/2009 | Troxler |
| 7,705,614 B2 | * | 4/2010 | Troxler et al. ........... 324/663 |
| 7,820,960 B2 | | 10/2010 | Troxler |
| 2003/0038634 A1 | | 2/2003 | Strack |
| 2003/0222662 A1 | | 12/2003 | Geisel |
| 2004/0095154 A1 | | 5/2004 | Lundstrom et al. |
| 2005/0150278 A1 | | 7/2005 | Troxler et al. |
| 2005/0267700 A1 | | 12/2005 | Gamache et al. |
| 2011/0035182 A1 | | 2/2011 | Troxler |

FOREIGN PATENT DOCUMENTS

| | | |
|---|---|---|
| GB | 1284295 | 8/1972 |
| WO | WO 02/03055 | 1/2002 |
| WO | WO 02/027760 | 3/2007 |
| WO | WO 2007/027797 | 3/2007 |

OTHER PUBLICATIONS

Official Action for Chinese Patent Application No. 200680040215.X (Dec. 18, 2009).

Notice of Allowance and Issue Fee(s) Due for U.S. Appl. No. 11/513,334 (Jun. 12, 2009).

Notice of Allowance and Issue Fee(s) Due for U.S. Appl. No. 11/512,732 (May 29, 2009).

Final Office Action for U.S. Appl. No. 11/513,334 (Oct. 30, 2008).

Official Action for U.S. Appl. No. 11/512,732 (Sep. 11, 2008).

Notification of Transmittal of International Preliminary Report on Patentability for International Application No. PCT/US2006/033898 (Jun. 23, 2008).

Notification of Transmittal of the International Search Report and The Written Opinion of the International Searching Authority, or the Declaration for International Application No. PCT/US2006/033839 (May 29, 2008).

Notification Concerning Trasmittal of International Preliminary Report on Patentability for International Application No. PCT/US2006/033898 (Mar. 13, 2008).

Official Action for U.S. Appl. No. 11/513,334 (Jan. 29, 2008).

International Preliminary Report on Patentability (Jun. 23, 2008).

Notification of Transmittal of the International Search Report and the Written Opinion of the International Searching Authority, or the Declaration of International Application No. PCT/US2006/033898 (Sep. 26, 2007).

Restriction Requirement for U.S. Appl. No. 11/513,334 (Sep. 13, 2007).

Sebesta et al., "New Technologies and Approaches to Controlling the Quality of Flexible Pavement Construction Performed in Cooperation with the Texas Department of Transportation and the Federal Highway Administration," Texas Transportation Institute, Report 0-4774-1 (Jun. 2006).

U.S. Department of the Army, "Engineering and Design Site Characterization and Analysis Penetrometer System (SCAPS)," EP 1110-1-32, pp. 1-14 (Nov. 1, 2005).

Kim et al., "Typical Dynamic Moduli for North Carolina Asphalt Concrete Mixtures," Final Report FWHA/NC, Mar. 2005 (May 2005).

Balendonck et al., "Sensors for Soil, Substrates, and Concrete Based on the MCM100 Microchip," Electromagnetic Aquametry, Springer (2005).

Chen et al., "A Correlation Between Dynamic Cone Penetrometer Values and Pavement Layer Moduli," Geotechnical Testing Journal, vol. 28, No. 1 (2005).

Daschner et al., "Determination of Composition of Foodstuffs Using MW Dielectric Spectra," Electromagnetic Aquametry, Springer, pp. 455-461 (2005).

Hauschild, "Density and Moisture Measurements Using Microwave Resonators," Electromagnetic Aquametry, Springer (2005).

Huebner et al., "Advanced Measurement Methods in Time Domain Reflectometry for Soil Moisture Determination," Electromagnetic Aquametry, Springer (2005).

Jones et al., "Thermal and Geometrical Effects on Bulk Permittivity of Porous Mixtures Containing Bound Water," Electromagnetc Aquametry, Springer (2005).

Kaatze, "Electromagnetic Wave Interactions with Water and Aqueous Solutions," Electromagnetic Aquametry, Springer (2005).

Kraszewski, "Recent Developments in Electromagnetic Aquametry," Electromagnetic Aquametry, Springer, pp. 6-11 (2005).

Kupfer, "Methods of Density-Independent Moisture Measurement," Electromagnetic Aquametry, Springer, pp. 135-165 (2005).

Kupfer, "Simulations and Experiments for Detection of Moisture Profiles with TDR in a Saline Environment," Electromagnetic Aquametry, Springer, pp. 349-365 (2005).

Sachs, "Principles of Ultra-Wideband Sensor Electronics," Electromagnetic Aquametry, Springer (2005).

Sihvola, "Model Systems for Materials with High Dielectric Losses in Aquametry," Electromagnetic Aquametry, Springer (2005).

Sovlukov, "Microwave and RF Resonator-Based Aquametry," Electromagnetic Aquametry, Springer (2005).

Stacheder et al., "Combined TDR and Low-Frequency Permittivity Measurements for Continuous Snow Wetness and Snow Density Determination," Electromagnetic Aquametry, Springer (2005).

Thakur, "Moisture Measurement in Multi-Layered Systems," Electromagnetic Aquametry, Springer (2005).

Wolter et al., "Moisture Measuring with Nuclear Magnetic Resonance (NMR)," Electromagnetic Aquametry, Springer (2005).

Zeghal et al., "Review of the New Mechanistic-Empirical Pavement Design Guide—A Material Characterization Perspective," Investing in New Materials, Products and Processes Session—2005 Annual Conference, Transportation Association of Canada, Calgary, Alberta (2005).

Hoffmann et al., "Stiffness Estimates Using Portable Deflectometers," TRB Annual Meeting 2004, Washington, D.C. (2004).

Olidis et al., "Guide for the Mechanistic-Empirical Design of New and Rehabilitated Pavement Structures Materials Characterization—Is Your Agency Ready?" Applied Research Associates, Inc.—ERES Consultants Division (2004).

Sun et al., "Evalutaion of a Combined Penetrometer for Simultaneous Measurement of Penetration Resistance and Soil Water Content," Journal of Plant Nutr. Soil Science, vol. 167, pp. 745-751 (2004).

Nazarian et al., "Quality Management of FLexible Pavement Layers with Seismic Methods," Center for Highway Materials Research, Research Report 1735-3F (Dec. 2002).

Nelson et al, "RF Sensing of Grain and Seed Moisture Content," IEEE Sensors_Journal, vol. 1, No. 2, pp. 119-126 (Aug. 2001).

Vaz et al., "Simultaneous Measurement of Soil Penetration Resistance and Water Content with a Combined Penetrometer-TDR Moisture Probe," Soil Soc. Am. Journal, vol. 65, pp. 4-12 (2001).

Nazarian et al., "Compaction Quality Control of Soils Using Wave Propagation Techniques," Center for Highway Materials Research, The University of Texas at El Paso, TRB 2001 Washington D.C. (Nov. 2000).

Newtson et al., "Nondestructive Evaluation Using Numerical Simulation of Impact Response," ACI Materials Journal (May-Jun. 2000).

Gucunski et al., "Seismic Methods in Post Construction Condition Monitoring of Bridge Decks," Use of Geophysical Methods in Construction, Proceedings Geo-Denver (2000).

Gucunski et al., "Am Backcalculation of Pavement Profiles from the SASW Test," Pavement Subgrade Unbound Materials and NonDestructive Testing, ED. M. Mamlouk, ASCE, Geo-Denver (2000).

Russell et al., "Design of Resilient Modulus of Subgrade Soils from FWD Tests," Pavement Subgrade Unbound Materials and NonDestructive Testing, ED. M. Mamlouk, ASCE, Geo-Denver (2000).

Nazarian et al., "Use of Instrumented Dynamic Cone Penetrometer in Pavement Characterization," Third International Symposium on Nondestructive Testing of_Pavements and Backcalculation of Moduli, ASTM Stock No. STP1375 (Jul. 1, 1999), pp. 214-228.

Chen et al., "Evaluation of In-Situ Resilient Modulus Testing Techniques," Recent Advances in the Characterization of Transportation Geo-Materials, ASCE, No. 89 (1999).

Newcomb et al., "Measuring In Situ Mechanical Properties of Pavement Subgrade Soils," Synthesis of Highway Practice 278, NCHRP, Washington DC (1999).

Sabburg et al., "Dielectric Behavior of Moist Swelling Clay Soils at Microwave Frequencies," IEEE Transactions on Geoscience and Remote Sensing, vol. 35, No. 3, pp. 784-787 (May 1997).

Lunne et al., "Cone Penetration Testing in Geotechnical Practice," Blackie Academic and Professional Publishing (1997).

Trabelsi et al., "New Density-Independent Calibration Function for Microwave Sensing of Moisture Content in Particulate Materials," IEEE Transactions on Instrumentation and Measurement, vol. 47, No. 3, pp. 613-622 (Jun. 1998).

Trabelsi et al., "A Microwave Method for On-Line Determination of Bulk Density and Moisture Content of Particulate Materials," IEEE Transactions on Instrumentation and Measurement, vol. 47, No. 1, pp. 127-132 (Feb. 1998).

Cutmore et al., "On-Line Measurement of Composition for the Australian Mineral and Energy Industries," IEEE Instrumentation and Measurement Technology Conference, Belgium, pp. 330-334 (Jun. 4-6, 1996).

Peplinski et al., "Dielectric Properties of Soils in the 0.3-1.3-GHz Range," IEEE Transactions on Geoscience and Remote Sensing, vol. 33, No. 3 (May 1995).

Vermeulen et al., "Continuous Measurement of Moisture in Nonconducting Materials," IEEE Transactions on Instrumentation and Measurement, vol. 41, No. 6, pp. 1023-1026 (Dec. 1992).

Scott et al., "Measured Electrical Constitutive Parameters of Soil as Functions of Frequencey and Moisture Content," IEEE Transactions on Geoscience and Remote Sensing, vol. 30, No. 3, pp. 621-623 (May 1992).

Thuery, "Microwaves: Industrial Scientific and Medical Applications," Artec House, (1992).

Kraszewski, "Microwave Aquametry—Needs and Perspectives," IEE MTT, vol. 39, No. 5, pp. 828-835 (May 1991).

Arulanandan, "Dielectric Method for Prediction of Porosity of Saturated Soil," Journal of Geotechnical Engineering, vol. 117, No. 2, pp. 319-330 (Feb. 1991).

Roesset et al., "Modulus and Thickness of the Pavement Surface Layer from SASW Tests," Transportation Research Record 1260 (1990).

Badu-Tweneboah et al., "Prediction of Flexible Pavement Layer Moduli from Dynaflect and FWD Deflections," Nondestructive Testing of Pavements and Backcalculation of Moduli, ASTM STP 1026 (1989).

Chou et al., "Backcalculation of Layer Moduli from Nondestructive Testing Pavement Deflection Data Using the Expert System Approach," Nondestructive Testing of Pavements and Backcalculation of Moduli, ASTM STP 1026 (1989).

Consentino et al., "FWD Backcalculated Moduli Compared with Pavement Pressuremeter Moduli and Cyclic Triaxial Moduli," Nondestructive Testing of Pavements and Backcalculation of Moduli, ASTM STP 1026 (1989).

Germann et al., "Temperature, Frequency, and Load Level Correction Factors for Backcalculated Moduli Values," Nondestructive Testing of Pavements and Backcalculation of Moduli, ASTM STP 1026 (1989).

Hiltunen et al., "Influence of Source and Receiver Geometry on the Testing of Pavements by the Surface Waves Method," Nondestructive Testing of Pavements and Backcalculation of Moduli, ASTM STP 1026 (1989).

Hossain et al., "Numerical and Optimization Techniques Applied to Surface Waves for Backcalculation of Layer Moduli," Nondestructive Testing of Pavements and Backcalculation of Moduli, ASTM STP 1026 (1989).

Lytton, "Backcalculation of Pavement Layer Properties," Nondestructive Testing of Pavements and Backcalculation of Moduli, ASTM STP 1026 (1989).

Nazarian et al., "Nondestructive Evaluation of Pavements by Surface Wave Method," Nondestructive Testing of Pavements and Backcalculation of Moduli, ASTM STP 1026 (1989).

Sayyedsadr et al., "SASWOPR: A Program to Operated on Spectral Analysis of Surface Wave Data," Nondestructive Testing of Pavements and Backcalculation of Moduli, ASTM STP 1026 (1989).

Uddin et al., "In Situ Material Properties from Dynamic Deflection Equipment," Nondestructive Testing of Pavements and Backcalculation of Moduli, ASTM STP 1026 (1989).

Powell et al., "Use of a Density-Independent Function and Microwave Measurement System for Grain Moisture and Measurement," Transactions of ASAE, vol. 31, No. 6 (Nov.-Dec. 1988).

Dean et al., "Soil Moisture Measurement by an Improved Capacitance Technique, Part 1, Sensor Design and Performance," Journal of Hydrology, vol. 93, pp. 67-78 (1987).

Shimin, "A New Method for Measuring Dielectric Constant Using the Resonant Ferquency of a Patch Antenna," IEEE MTT—34, No. 9, pp. 923-931 (Sep. 1986).

Lew et al., "Relationships Between Shear Wave Velocity and Depth of Overburden," Measurement and Use of Shear Wave Velocity for Evalutating Dynamic Soil Properties, ASCE (1985).

Robertson et al., "Seismic CPT to Measure In-Situ Shear Wave Velocity," Measurement and Use of Shear Wave Velocity for Evalutating Dynamic Soil Properties, ASCE (1985).

Stokoe et al., "Use of Rayleigh Waves in Liquefaction Studies," Measurement and Use of Shear Wave Velocity for Evaluating Dynamic Soil Properties, ASCE (1985).

Stoll, "Computer-Aided Studies of Complex Soil Moduli," Measurement and Use of Shear Wave Velocity for Evaluating Dynamic Soil Properties, ASCE (1985).

Heisey et al., "Moduli of Pavement Systems from Spectral Analysis of Surface Waves", Transportation Research Record 852 (1983).

Kuraz, "Testing of a Field Dielectric Soil Moisture Meter," Geotechnical Testing Journal, vol. 4, No. 3, pp. 111-116 (Sep. 1981).

Meyer et al., "Feasibility Study of Density-Independent Moisture Measurement with Microwaves," IEEE MTT-29 pp. 732-739 (Jul. 1981).

Holtz "Introduction to Geotechnical Engineering" Prentice Hall (1981).

Topp, "Electromagnetic Determination of Soil Water Content: Measurements in Coaxial Transmission Lines," Water Resources Research, vol. 16, No. 3, pp. 574-582 (Jun. 1980).

Wobschall, "A Frequency Shift Dielectric Soil Moisture Sensor," IEEE Transactions of Geoscience Electronics, vol. GE-16, No. 2 (Apr. 1978).

Kraszewski et al., "A Preliminary Study on Microwave Monitoring of Moisture Content in Wheat," Journal of Microwave Power, vol. 12, No. 3, pp. 241-255 (Sep. 1977).

Drnevich et al., "Modulus and Damping of Soils by the Resonant Column Method," Dynamic Geotechnical Testing, ASTM STP 654, Denver, CO (Jun. 1977).

Hoar et al., "Generation and Measurement of Shear Waves In Situ," Dynamic Geotechnical Testing, ASTM STP 654, Denver, CO (Jun. 1977).

McLamore et al., "Crooshole Testing Using Explosive and Mechanical Energy Sources," Dynamic Geotechnical Testing, ASTM STP 654, pp. 30-55 (Jun. 1977).

Statton et al., "In Situ Seismic Shear-Wave Velocity Measurements and Proposed Procedures," Dynamic Geotechnical Testing, ASTM STP 654, Denver, CO (Jun. 1977).

Stephenson, "Ultrasonic Testing for Determining Dynamic Soil Moduli," Dynamic Geotechnical Testing, ASTM STP 654, Denver, CO (Jun. 1977).

Wobschall, "A Theory of the Complex Dielectric Permittivity of Soil Containing Water," IEEE Transactions on Geoscience Electron, vol. GE-15, No. 1, pp. 49-58 (1977).

Anderson et al., "Comparison of Field and Laboratory Shear Moduli," In Situ Measurement of Soil Properties, vol. I, North Carolina State University, Raleigh, NC, ASCE (Jun. 1-4, 1975).

Miller et al., "In Situ Impulse Test for Dynamic Shear Modulus of Soils." In Situ Measurement of Soil Properties, vol. I, North Carolina State University, Raleigh, NC, ASCE 1975 (Jun. 1-4, 1975).

Stokoe et al., "Shear Moduli of Two Compacted Fills," In Situ Measurement of Soil Properties, vol. I, North Carolina State University, Raleigh, NC, ASCE (Jun. 1-4, 1975).

Windle et al., "Electrical Resistivity Methof for Determining Volume Changes that Occur During a Pressuremeter Test," In Situ Measurementof Soil Properties, vol. I, North Carolina State University, Raleigh, NC, ASCE 1975 (Jun. 1-4, 1975).

Wissa et al., "The Piezometer Probe," In Situ Measurement of Soil Properties, vol. I, North Carolina State University, Raleigh, NC, ASCE 1975 (Jul. 1-4, 1975).

Birchak et al., "High Dielectric Constant Microwave Probes for Sensing Soil Moisture," Proceedings of the IEEE, vol. 62, No. 1, pp. 93-98 (Jan. 1974).

Hipp, "Soil Electromagnetic Parameters as Functions of Frequency, Soil Density and Soil Moisture," Proceedings of the IEEE, vol. 62, No. 1, pp. 98-103 (Jan. 1974).

Hoekstra et al., "Dielectric Properties of Soils at UHF and Microwave Frequencies," Journal of Geophysical Research, vol. 79, pp. 1699-1708 (1974).

Henkel, "The Relationships Between the Effective Stresses and Water Content in Saturated Clays," Geotechnique, vol. 10 (1960).

Henkel, "The Shear Strength of Saturated Remolded Clays," Proceedings of Research Conference on Shear Strength of Cohesive Soils, ASCE, pp. 533-554 (1960).

Benson, "An Overview of Geophysical and Non-Destructive Methods for Characterization of Roads and Bridges," Use of Geophysical Methods in Construction, ASCE, 108 (Publication Date Unknown).

Bose et al., "Dielectric Relaxation Study of Water and Water/Oil Microemulsion System," Microwave Aquametry—Electromagnetic Wave Interaction with Water-Containing Minerals, IEEE (Publication Date Unknown).

Brandelik et al., "Measurement of Bound and Free Water in Mixtures," Microwave Aquametry—Electromagnetic Wave Interantion with Water-Containing Materials, IEEE (Publication Date Unknown).

Gentili et al., "Analysis of Electromagnetic Sensors for Dielectric Spectroscopy by Using the $(FD)^2TD$ Method," Microwave Aquametry—Electromagnetic Wave Interaction with Water-Containing Material, IEEE (Publication Date Unknown).

Gentili et al., "An Integrated Microwave Moisture Sensor," Microwave Aquametry—Electromagnetic Wave Interactionwith Water-Containing Materials, IEEE (Publication Date Unknown).

Griffin et al., "Precision of Seismic Wave Proagation Methods in Construction Applications," Use of Geophysical Methods in Construction, ASCE, 108 (Publication Date Unknown).

Guzina, "Dynamic Soil Sensing via Horizontally-Polarized Shear Waves," Use of Geophysical Methods in Construction, ASCE, 108 (Publication Date Unknown).

Guzina et al., "Verification and Enhancement of Portable Deflectometer Devices," http://www.mrr.dot.state.mn.us/research/MnROAD_Project/workshop2003/Base_Subgrade_Characterization_Devices.pdf (Publication Date Unknown).

Jung, "Application of Electrical Resistivity Imaging Techniques to Civil & Environmental Problems," Use of Geophysical Methods in Construction, ASCE, 108 (Publication Date Unknown).

Kaatze "Microwave Dielectric Properties of Water," Microwave Aquametry—Electromagnetic Wave Interaction with Water-Containing Materials, IEEE (Publication Date Unknown).

Kendra et al., "Snow Probe for in Situ Determination of Wetness and Density,"_Microwave Aquametry—Electromagnetic Wave Interaction with Water-Containg_Materials, IEEE (Publication Date Unknown).

King et al., "Material Characterization Using of Microwave Open Reflection Resonator Sensors," Microwave Aquametry—Electromagnetic Wave Interaction with Water-Containing Materials, IEEE (Publication Date Unknown).

Kobayashi et al., "Microwave Attenuation in a Wet Layer of Limestone," Microwave Aquamentry—Electromagnetic Wave Interaction with Water-Containg Materials, IEEE (Publication Date Unknown).

Kraszewski, "Microwave Aquametry: Introduction to the Workshop," Microwave Aquametry—Electromagnetic Wave Interaction with Water-Containing Materials, IEEE (Publication Date Unknown).

Kraszewski et al., "Moisture Content Determination in Single Kernels and Seeds with Microwave Resonant Sensors," Microwave Aquametry—Electromagnetic Wave Interaction with Water-Containing Materials, IEEE (Publication Date Unknown).

Kupfer, "Possibilities and Limitations of Density-Independent Moisture Measurement with Microwaves," Microwave Aquametry—Electromagnetic Wave Interaction with Water-Containing Materials, IEEE, pp. 313-327 (Publication Date Unknown).

Lin et al., "Time Domain Reflectometry for Compaction Quality Control," Use of Geophysical Methods in Construction, ASCE, 108 (Publication Date Unknown).

Mashimo, "Free and Bound Water in Various Matrix Systems Studied by Advanced Microwave Techniques," Microwave Aquametry—Electromagnetic Wave Interaction with Water-Containing Materials, IEEE, pp. 93-99 (Publication Date Unknown).

Robinson et al., "Single- and Multiple-Frequency Phase Change Methods for Microwave Moisture Measurement," Microwave Aquametry—Electromagnetic Wave Interaction with Water-Containing Materials, IEEE (Publication Date Unknown).

Sihvola, "Dielectric Mixture Theories in Permittivity prediction: Effects of Water on Macroscopic Parameters," Microwave Aquametry—Electromagnetic Wave Interaction with Water-Containing Materials, IEEE (Publication Date Unknown).

Volgyi, "Integrated Microwave Moisture Sensors for Automatic Process Control," Microwave Aquametry—Electromagnetic Wave Interaction with Water-Containing_Materials, IEEE, pp.223-228 (Publication Date Unknown).

Walker, "Accurate Percent Water Determination by Microwave Interaction Alone; 1954-Present," Microwave Aquametry—Electromagnetic Wave Interaction with Water-Containing Materials, IEEE (Publication Date Unknown).

Wang et al., "SH-Wave Refraction/Reflection and Site Characterization," Use of Geophysical Methods in Construction, ASCE, 108 (Publication Date Unknown).

Xu et al., "Calculation of Sensitivity of Various Coaxial Sensors Used in Microwave Permittivity Measurements," Microwave Aquametry—Electromagnetic Wave Interaction with Water-Containing Materials, IEEE (Publication Date Unknown).

Notice of Allowance and Fee(s) Due for U.S. Appl. No. 12/534,739 (Jun. 17, 2010).

Supplementary European Search Report for European Patent No. 1932020 (Jan. 20, 2011).

Notice of Allowance and Fee(s) Due for U.S. Appl. No. 12/910,745 (Dec. 13, 2010).

* cited by examiner

METHODS, SYSTEMS, AND COMPUTER PROGRAM PRODUCTS FOR DETERMINING A PROPERTY OF CONSTRUCTION MATERIAL

CROSS-REFERENCE TO RELATED APPLICATIONS

This application is a divisional of U.S. patent application Ser. No. 11/513,334, filed Aug. 30, 2006, now U.S. Pat. No. 7,581,446, which claims the benefit of U.S. Provisional Patent Application Ser. No. 60/712,754, filed Aug. 30, 2005, and U.S. Provisional Patent Application Ser. No. 60/719,071, filed Sep. 21, 2005, the disclosures of which are incorporated by reference herein in their entireties. The disclosure of U.S. patent application Ser. No. 11/512,732 (now U.S. Pat. No. 7,569,810), filed Aug. 30, 2006, is incorporated by reference in its entirety.

TECHNICAL FIELD

The subject matter described herein relates to measuring material properties. More particularly, the subject matter described herein relates to methods, systems, and computer program products for determining a property of construction material.

BACKGROUND

An important aspect of construction engineering is road construction and maintenance. The ability to design and construct roads based on future loads and environmental factors is very important as it saves time, effort, and resources in future maintenance costs. A well-designed road will have long-term performance when the design factors of loading, climatic, and soil conditions are accounted for properly.

In construction engineering, some of the most important properties of interest are volumetric and mechanistic properties of construction materials such as soil, asphalt, concrete, and the like. In particular, there are procedures in construction engineering practice that relate total volume $V_t$, mass of water $M_w$, and mass of dry solids $M_s$ to the performance of a structure built on a soils foundation. Other important properties of interest are mechanical properties such as stiffness, modulus, and density. Thus, the measurements of these properties are important for construction engineering.

Asphalt and cement mixes used for construction typically remain relatively homogeneous and are well behaved unless problems such as segregation arise. In general, well-controlled materials can provide for the ability to calibrate non-nuclear and nuclear surface gauges with relatively good confidence. On the other hand, in most geographic areas, soils are inhomogeneous, and the earthwork required to excavate and fill on construction projects typically leads to areas and layers of soil of different mineralogy, moisture content, gradation, and texture. The result is that indirect methods of measurement, such as surface electromagnetic or acoustic instruments, frequently need recalibration when the operator suspects something in the base construction material has changed.

One of the most robust construction material measurement tools currently available is a nuclear density gauge. However, even this equipment is susceptible to limited errors as a result of the chemical composition effects. The largest error for nuclear techniques is in the water content which is used to correct the wet density measurement. If the composition under the gauge becomes richer in hydrogen than the original calibration site, then recalibration is necessary. For instance mica loaded clay and sand-like materials have different chemical compositions, and would need different moisture offsets or corrections. The problem comes when the clay/sand or mineral content varies throughout the scope of the project.

It is the purpose of the semi-empirical and mechanistic design methods to link laboratory tests and design criteria with the material work in the field. For instance, if a soil fails a laboratory resilient modulus (RM) test, the soil could be replaced with fill or strengthened with lime or cement. In the field, the soils are not typically homogenous, and can change as a result of climatic conditions such as temperature and moisture. For this reason, it is desirable to have quality control instrumentation and methods that can adjust for temperature and/or moisture effects. The results of such data can be helpful to construction personnel for determining soil and asphalt areas of low quality.

Techniques are known for measuring the modulus of construction materials. Generally, the measurements are obtained by generating an acoustic disturbance in the construction material and measuring a response of the material to the disturbance. For example, wave velocities of the response to the acoustic disturbance may be measured for determining modulus. However, the determined modulus in these techniques are subject to inaccuracies. It is desirable for providing correction to modulus measurements and generally improving the accuracy of modulus measurements of construction material.

Accordingly, in light of the above described difficulties and needs associated with nuclear density gauges, there exists a need for improved methods, systems, and computer program products for a property of construction material.

SUMMARY

According to one aspect, the subject matter described herein includes methods, systems, and computer program products for determining a property of construction material. According to one aspect, a material property gauge may be operable to determine a property of construction material. The gauge may include an electromagnetic sensor operable to measure a response of construction material to an electromagnetic field. Further, the electromagnetic sensor may be operable to produce a signal representing the measured response by the construction material to the electromagnetic field. An acoustic detector may be operable to detect a response of the construction material to the acoustical energy. Further, the acoustic detector may be operable to produce a signal representing the detected response by the construction material to the acoustical energy. A material property calculation function may be configured to calculate a property value associated with the construction material based upon the signals produced by the electromagnetic sensor and the acoustic detector.

According to another aspect, a material property gauge may include an electromagnetic sensor operable to measure a response of construction material to an electromagnetic field and operable to produce a signal representing the measured response by the construction material to the electromagnetic field. Further, the gauge may include a temperature sensor operable to measure a temperature associated with the construction material and operable to produce a signal representing the measured temperature associated with the construction material. A material property calculation function may be configured to calculate a property value associated with the construction material based upon the signals produced by the electromagnetic sensor and the temperature sensor.

As used herein, the terms "sample construction material," "sample material," and "construction material" refer to any suitable material used in a construction process. Exemplary sample construction materials include soil, asphalt, pavement, stone, sub-base material, sub-grade material, cement, agricultural soils, batch plants, concrete curing rate, concrete chloride inclusion, sodium chloride content, concrete delamination, water content, water-cement materials, alkali-silica, various soils, flexible asphalt, and any combination thereof.

As used herein, the terms "electromagnetic field generator" and "electromagnetic field source" refer to any suitable device or component operable to generate an electromagnetic field. Exemplary electromagnetic field generators include a voltage controlled oscillator (VCO), a Clapp oscillator, a relaxation oscillator, a ring oscillator, an RC oscillator, a crystal oscillator, a blocking oscillator, a phase-locked oscillator, a voltage oscillator, a multivibrator, a Gunn diode, a numerically-controlled oscillator, a Kystron tube, a high-power microwave magnetron, a backward wave oscillator, a VLF transmitter, an integrated circuit timer, an arbitrary waveform generator, a pulse-wide modulation device, an analog synthesizer, current sources, synthesized sources, YIG-tuned oscillators, and integrated circuits.

As used herein, the terms "acoustic generator" and "acoustic source" refer to any suitable device or component operable to generate acoustic energy. Exemplary acoustic generators include a penetrometer, a Clegg Hammer, a falling weight deflectometer, a Briaud compaction device, and an FWD, a geophone, an accelerometer, a vibration sensor, a piezoelectric device, an inductive coil-based device, a magnetostrictive device, a bender element, and micro-electro-mechanical system (MEMS)-based device electromechanical shakers, solenoid activated hammers, instrumented hammers, frequency domain devices, and time domain devices.

The subject matter described herein may be implemented using a computer program product comprising computer executable instructions embodied in a computer-readable medium. Exemplary computer-readable media suitable for implementing the subject matter described herein include chip memory devices, disk memory devices, programmable logic devices, application specific integrated circuits, and downloadable electrical signals. In addition, a computer-readable medium that implements the subject matter described herein may be located on a single device or computing platform or may be distributed across multiple devices or computing platforms.

BRIEF DESCRIPTION OF THE DRAWINGS

Preferred embodiments of the subject matter described herein will now be explained with reference to the accompanying drawings of which.

DETAILED DESCRIPTION

Figure 1A:
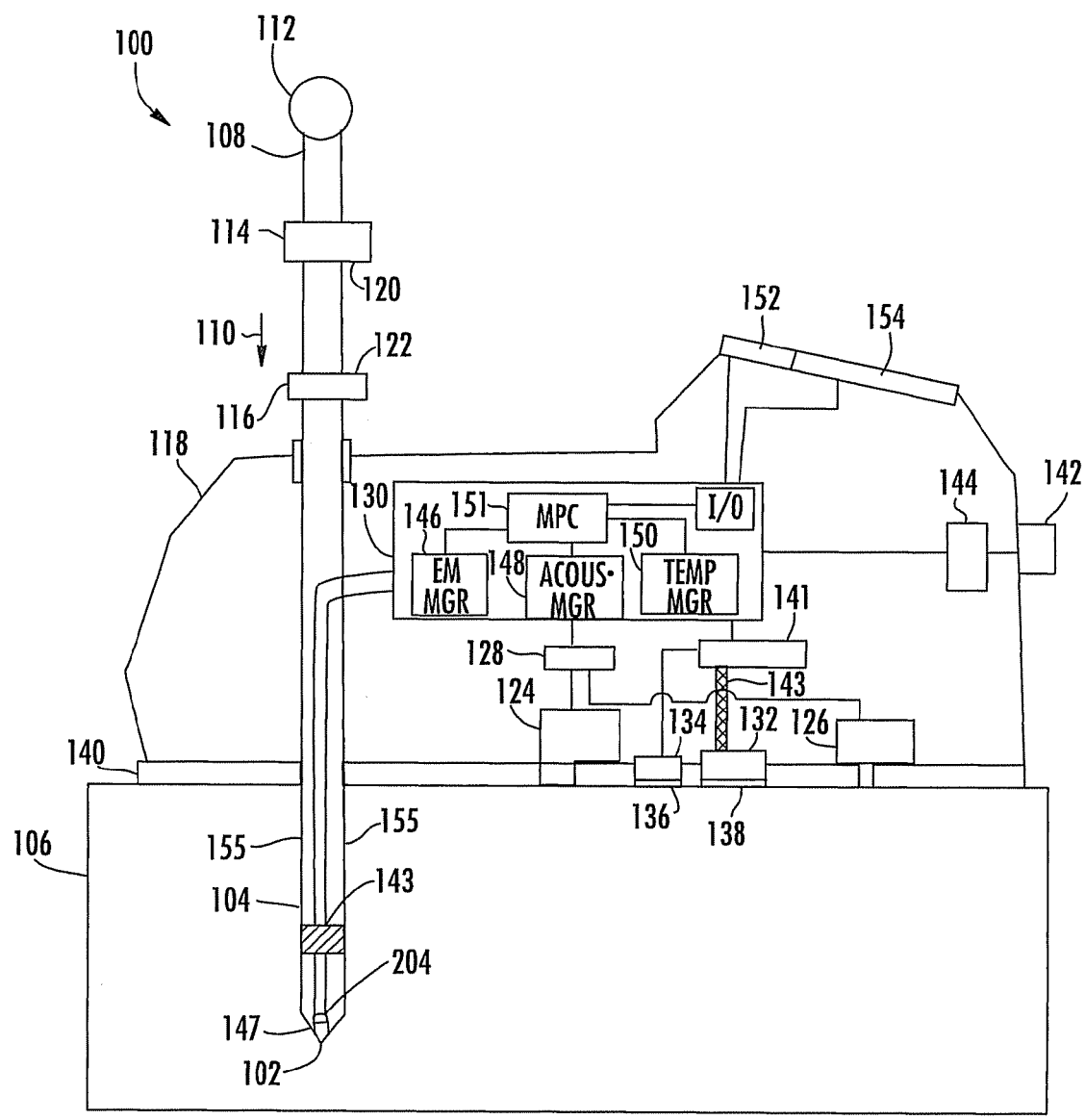
FIG. 1A is a vertical cross-sectional view of a material property gauge for measuring the density or modulus of material according to an embodiment of the subject matter described herein.

The subject matter described herein includes methods, systems, and computer program products for determining a property of construction material and/or various other materials. In one embodiment, the methods, systems, and computer program products described herein may determine a property value associated with a construction material under test. Exemplary construction materials include asphalt, soil, concrete, aggregate, and the like. Exemplary property values that may be determined include moisture content, Poisson ratio, modulus, shear strength, density, void content, and the like. According to one aspect, a material property gauge may include an electromagnetic sensor operable to measure a response of construction material to an electromagnetic field. The electromagnetic sensor may produce a signal representing the measured response by the construction material to the electromagnetic field. An acoustic detector may detect a response of the construction material to acoustical energy. Further, the acoustic detector may produce a signal representing the detected response by the construction material to the acoustical energy. A material property calculation function configured to calculate a property value associated with the construction material based upon the signals produced by the electromagnetic sensor and the acoustic detector. In one example, a material property calculation function may use a moisture content measurement for correcting determined property values of construction material.

Another important factor affecting the modulus of construction material includes temperature, particularly with asphalt. In another embodiment of the subject matter described herein, material property gauges and related methods are provided for using temperature measurements in material property calculations, particularly for making corrections to determined property values of construction material. According to one aspect, a material property gauge may include an electromagnetic sensor operable to measure a response of construction material to an electromagnetic field. The electromagnetic sensor may produce a signal representing the measured response by the construction material to the electromagnetic field. A temperature detector may correct a response of the construction material to acoustic or electromagnetic energy. A material property calculation function configured to calculate a property value associated with the construction material based upon the signals produced by the electromagnetic sensor and the temperature detector.

In one example of a property of interest in road construction engineering, mechanistic design methods characterize pavement based on its elastic response to a vehicular load. In this example, the pavement structure may be composed of asphaltic material or concrete surface, base, and subgrade, each having a material thickness t and characterized by the elastic modulus E, Poisson ratio v, and aggregate interface friction f. This results in a layered elastic system that can be analyzed using engineering mechanics. As a result, design and performance can be estimated from computations or measured stress and strains on each layer resulting in a systematic design and predicted response from the surface.

Mineralogy, degree of saturation, void ratio, gradation, texture, and soil fabric have important effects on the strength or modulus of soil. Further, for flexible pavements, the asphalt content, voids filled with asphalt (VFA), voids in mineral aggregate (VMA), binder modulus, temperature, and frequency of the load affect the modulus of the asphalt. The nuclear-based and electromagnetic-based measurements may be used for calculating the asphalt content, voids in surface pavement, moisture ratio of soil, and void ratio of soil. These volumetric parameters are related to the elastic response of a soil, asphalt, or pavement structure.

In one embodiment, the material property gauges according to the subject matter described herein may comprise an integrated and portable device. Further, the material property gauges may be operable in either in a backscatter mode or in both a backscatter mode and a transmission mode, as described in further detail herein. In one example of a gauge capable of transmission mode, the gauge may include a radiation source that is vertically moveable from a backscatter position, where it resides within the gauge housing, to a series of transmission positions, where it is inserted into holes or bores in the sample material. Nuclear gauges capable of measuring the density of sample materials have been developed by the assignee of the present subject matter. For example, nuclear gauges for measuring the density of sample materials are disclosed in U.S. Pat. Nos. 4,641,030; 4,701,868; and 6,310,936, all of which are incorporated herein by reference in their entirety.

FIG. 1A is a vertical cross-sectional view of a material property gauge 100 for measuring the density or modulus of material according to an embodiment of the subject matter described herein. Gauge 100 is operable to accurately determine a property value of a construction material, such as soil, asphalt, or any other suitable construction and/or paving material. Exemplary property values that may be determined by gauge 100 include mechanistic values, volumetric values, and moisture content values. Gauge 100 may measure a property value of soil in a transmission mode and measure a property value of asphalt in a backscatter mode. Gauge 100 has multi-functional use in that, with proper calibration, the gauge may be used for the in-situ measurements of moisture and density (and moisture and modulus) of construction materials, such as soils, asphalt, concrete, and the like.

Referring to FIG. 1A, gauge 100 is shown in a transmission mode, in which a tip end 102 of penetrometer 104 is positioned in an interior of a construction material 106. Penetrometer 104 may be adapted for generating acoustical energy in the interior of construction material 106 for detection of a response by construction material 106 to the acoustical energy. An operator of gauge 100 may manually generate the acoustical energy by moving an end 108 of penetrometer 104 distal tip end 102 in a vertical downward direction (indicated by direction arrow 110) towards the interior of construction material 106. Penetrometer end 108 may include a knob 112 for grip by the operator. A hammer component 114 may be fixedly attached to penetrometer end 108 such that the movement of component 114 corresponds to the movement of penetrometer end 108.

An acoustic anvil component 116 may be fixedly attached to tip end 102. Anvil component 116 and tip end 102 may be fixed with respect to gauge housing 118 in the transmission mode. Further, penetrometer end 108 and hammer component 114 may freely move with respect to anvil component 116 and tip end 102 such that a bottom surface 120 of hammer component 114 may contact a top surface 122 of anvil component 116 to generate acoustical energy. The acoustical energy may propagate the length of penetrometer 104 to tip end 102. The generated acoustical energy may also propagate into construction material 106.

In one embodiment, a penetrometer may be integrated into the gauge that includes a dual mass hammer. The dual mass hammer may include a first hammer of large mass for use in initial penetration of construction material. Further, the dual mass hammer may include a second hammer of smaller mass for use in generating an acoustical disturbance. Other exemplary devices for use with a penetrometer to generate acoustical energy include piezoelectronic sources, shakers, bender elements, and the like.

Gauge 100 may include one or more acoustic detectors 124 and 126 operable to detect the response of construction material 106 to the acoustical energy and operable to produce one or more signals representing the detected response by construction material 106 to the acoustical energy. In particular, acoustic detector 124 may be an accelerometer or geophone adapted for detecting acoustical energy propagating in a vertical direction. Acoustic detector 126 may be an accelerometer or geophone adapted for detecting acoustical energy propagating in a horizontal direction. Accelerometers are available by, for example, Endevco Corporation, of San Juan Capistrono, Calif.

The acoustical energy detected by acoustic detectors 124 and 126 may be acoustical energy produced by construction material 106 in response to the acoustical energy produced by penetrometer 104. Acoustic detectors 124 and 126 may be capable of wide band frequency response from several hertz to 100 kHz. In response to detecting acoustical energy, acoustic detectors 124 and 126 may generate electrical signals representing the acoustical energy and communicate the electrical signals to a printed circuit board (PCB) 128 configured to process the electrical signals and/or store data representative of the detected acoustical energy. Further, PCB 128 may include hardware, software, and/or firmware components suitable for receiving, processing, and transmitting electrical signals and suitable for storing data representative of values represented by the electrical signals. PCB 128 may communicate electrical signals representative of the detected acoustical energy to another PCB 130 for further processing and for use in determining a property value associated with construction material 106, as described in further detail herein.

Figure 1B:
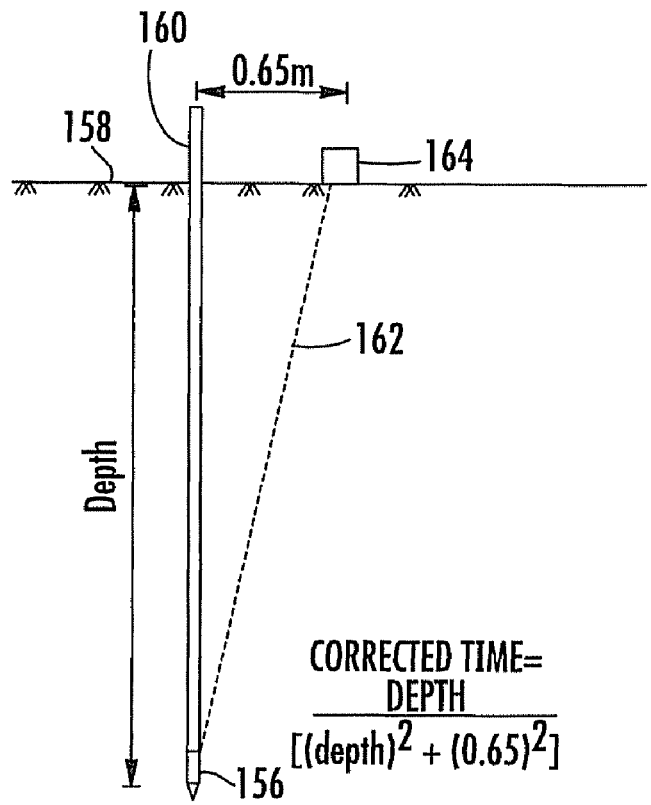
FIG. 1B is a schematic diagram illustrating a use of an exemplary acoustic source and an exemplary acoustic detector for determining a density and modulus of a sample material.
Figure 1C:
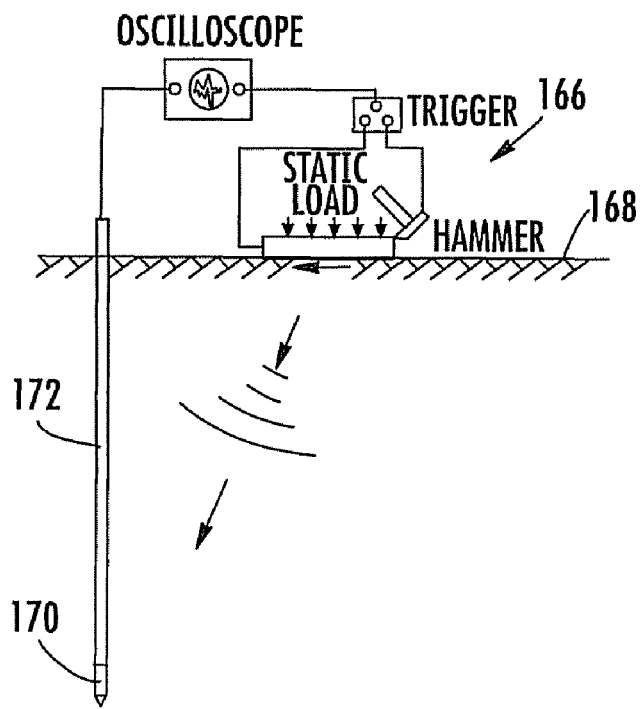
FIG. 1C is schematic diagram illustrating use of an exemplary acoustic source and an exemplary acoustic detector for determining a density and modulus of a sample material.

FIGS. 1B and 1C are schematic diagrams illustrating the use of an acoustic source and an acoustic detector for determining a density and modulus of a sample material. Referring to FIG. 1B, an acoustic source 156 may be inserted into a sample material 158 to a known depth by a penetrometer 160. Acoustic energy may travel a path 162 to an acoustic detector 164. The time of flight for the acoustic energy may be determined based on initiation of the acoustic energy by penetrometer 160 and the time that the acoustic energy is detected at detector 164. Further, the distance of path 162 may be estimated based on the known depth and the distance between the penetrometer entry point on the surface of sample material 158 and the position of detector 164. The distance of path 162 and time of flight data may be used for estimating a phase velocity. Based on elastic theory, the phase velocity can be used for determining a density and modulus of sample material 158.

Referring to FIG. 1C, in a similar manner to the system shown in FIG. 1B, the system shown in 1C includes an acoustic source 166 for directing acoustical energy into a sample material 168, and an acoustic detector 170 for detecting the response of sample material 168 to the acoustical energy. Further, a density or modulus of sample material 168 may be detected based on a path distance between source 166 and detector 170 and a determined time of flight of the acoustical energy. The system of FIG. 1C is different than the system shown in FIG. 1B in that acoustic detector 170 is positioned at an end of a penetrometer 172 and acoustic source 166 is positioned at a surface of sample material 168.

Figure 1D:
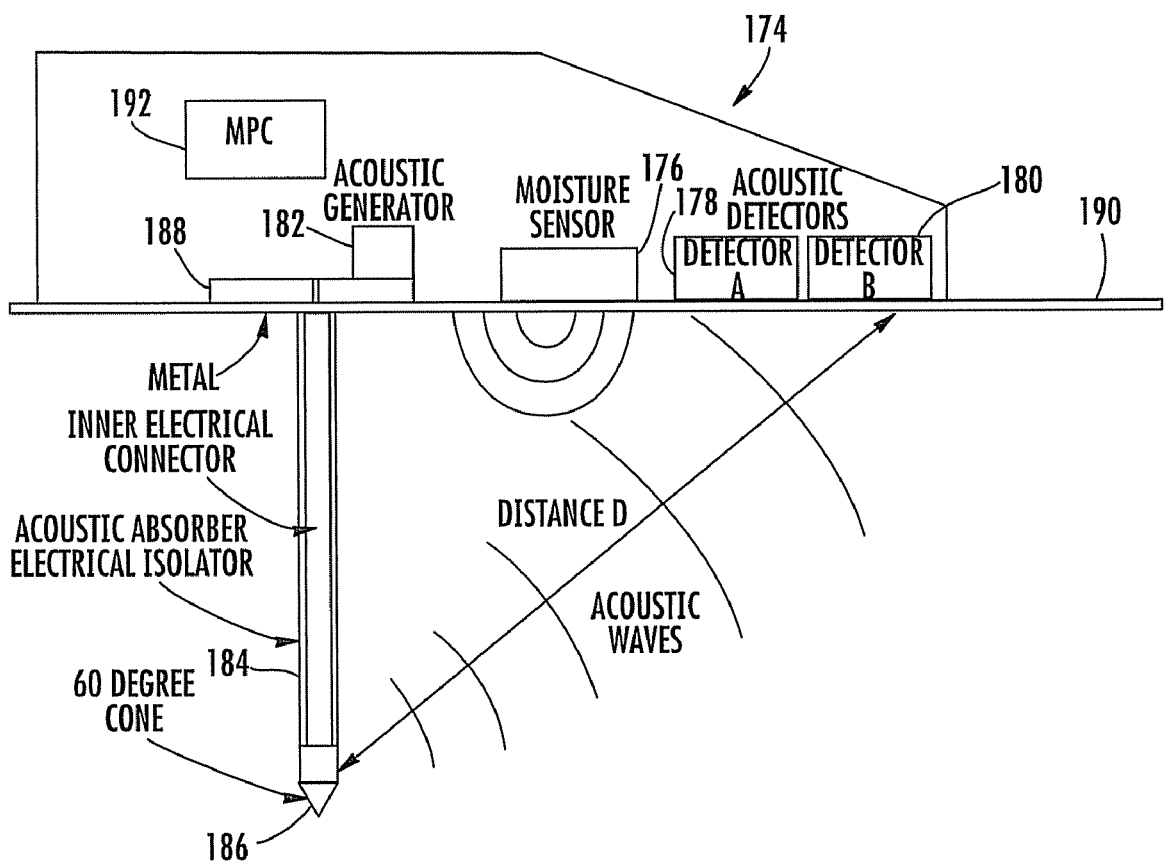
FIG. 1D is a schematic diagram of an exemplary material property gauge including a moisture sensor, a pair of acoustic detectors, an acoustic generator, and a penetrometer according to one embodiment of the subject matter described herein.

FIG. 1D illustrates a schematic diagram of an exemplary material property gauge 174 including a moisture sensor 176, a pair of acoustic detectors 178 and 180, an acoustic generator 182, and a penetrometer 184 according to one embodiment of the subject matter described herein. Referring to FIG. 1D, acoustic generator 182 may generate acoustical energy, which is transmitted to a 60° cone tip end 186 of penetrometer 184. In this example, acoustic generator 182 is rigidly affixed to a metal ring 188, which is affixed to penetrometer 184. The acoustical energy may emit from tip end 186 into a sample material 190 and be received by detectors 178 and 180 for use in sample material property value calculations by an MPC 190. The data may be used for density calculations or modulus calculations. Exemplary acoustic generators include magnetostrictive elements, piezoelectric-based devices, electrodynamic devices, and micro-electromechanical systems (MEMS)-based devices. Further, suitable acoustic generators include bender elements produced by GDS Instruments, of London, United Kingdom. Another exemplary acoustic generator includes a device having piezoelectric materials positioned between materials that bend upon excitement from the piezoelectric materials, magnetostrictive materials and the like.

Further, moisture sensor 176 may be operable to detect a moisture content of sample material 190. Data representing the detected moisture content may be communicated to an MPC 192. The moisture content data may be used for correcting density calculations.

Referring again to FIG. 1A, gauge 100 may include an electromagnetic sensor 132 operable to measure a response of construction material 106 to an electromagnetic field and operable to produce an electrical signal representative of the measured response by construction material 106 to the electromagnetic field. For example, electromagnetic sensor 132 may be operable to measure a permittivity, resistivity, a dielectric constant, and/or a conductivity of sample material 106.

In this example, gauge 100 may include an electromagnetic field source 134 operable to generate an electromagnetic field and be positioned near a surface of construction material 106 such that the electromagnetic field extends into construction material 106. Alternatively, signal source 134 and/or sensor 132 may be positioned within an interior of sample material 212. In one embodiment, gauge 100 may include a component operable in a self-impedance mode, wherein terminal impedance of the component is measured as it is powered, and the terminal or driving point impedance changes as the permittivity increases.

Electromagnetic sensor 132 may detect at least a portion of the electromagnetic field from construction material 106 that was produced by signal source 134. A frequency and/or time domain technique may be used for determining a property value of construction material 106. The electromagnetic field may range from static (DC) to microwave. Exemplary frequency techniques for use in determining a moisture property include using fringing field capacitors to produce an electromagnetic field; time domain reflectometry techniques; single-frequency techniques; sweeping-frequency techniques; microwave absorption techniques; and microwave phase shift techniques. Further, suitable moisture signal detectors include detectors operable to measure the real and imaginary parts of a dielectric constant at a single frequency, multiple frequencies, continuous sweeps of frequencies, and/ or chirps of frequency content. In the time domain, direct steps or pulses may be produced by a signal source and detected by a detector for determining a property value. Further, a fast Fourier transform (FFT) technique may be applied to the frequency and time domains for determining a property value. Further, an orthogonal or bi-orthogonal basis decomposition technique may be applied to the frequency and time domains (such as a fast Fourier transform (FFT), wavelet transform, or wave-packet decomposition) for determining a property value. The conductivity and permittivity of construction material 106 may be determined based on the detected electromagnetic field. In one example, the conductivity and permittivity may be used for determining a moisture property of construction material 106.

Gauge 100 may include a source window 136 and a receiver window 138 associated with source 134 and sensor 132, respectively. Source window 136 and receiver window 138 may extend through a base plate 140 such that electromagnetic fields may pass through base plate 140 and between source 134 and sensor 132. Exemplary window materials include aluminum oxide, sapphire, ceramics, plastics, and suitable insulators.

Another electromagnetic sensor 143 may be positioned within penetrometer 104 for detecting an electromagnetic field of construction material 106. Sensor 143 may be positioned near end 102 of penetrometer 104 such that sensor 143 is positioned within construction material 106 in the transmission mode. In one example, sensor 143 may be a capacitance sensor operable to measure a moisture property of construction material 106 at a predetermined depth with respect to the top surface of construction material 106. Sensor 143 may communicate an electrical signal representative of the measurement to PCB 130 for processing and use in determining a property value associated with construction material 106.

A PCB 141 may be in operable communication with source 134 and sensor 132. PCB 141 may include suitable hardware, software, and/or firmware components for control of source 134 and sensor 132. In particular, PCB 141 may control source 134 to generate an electromagnetic field. For example, PCB 141 may supply power to circuitry of source 134 for generating a predetermined electromagnetic field. Further, PCB 141 may be operable to receive a signal from sensor 132 representing detected electromagnetic fields via a coaxial cable 143. In one example, PCB 141 may determine a moisture property of sample material 106 based on the signal representation.

Figure 8:
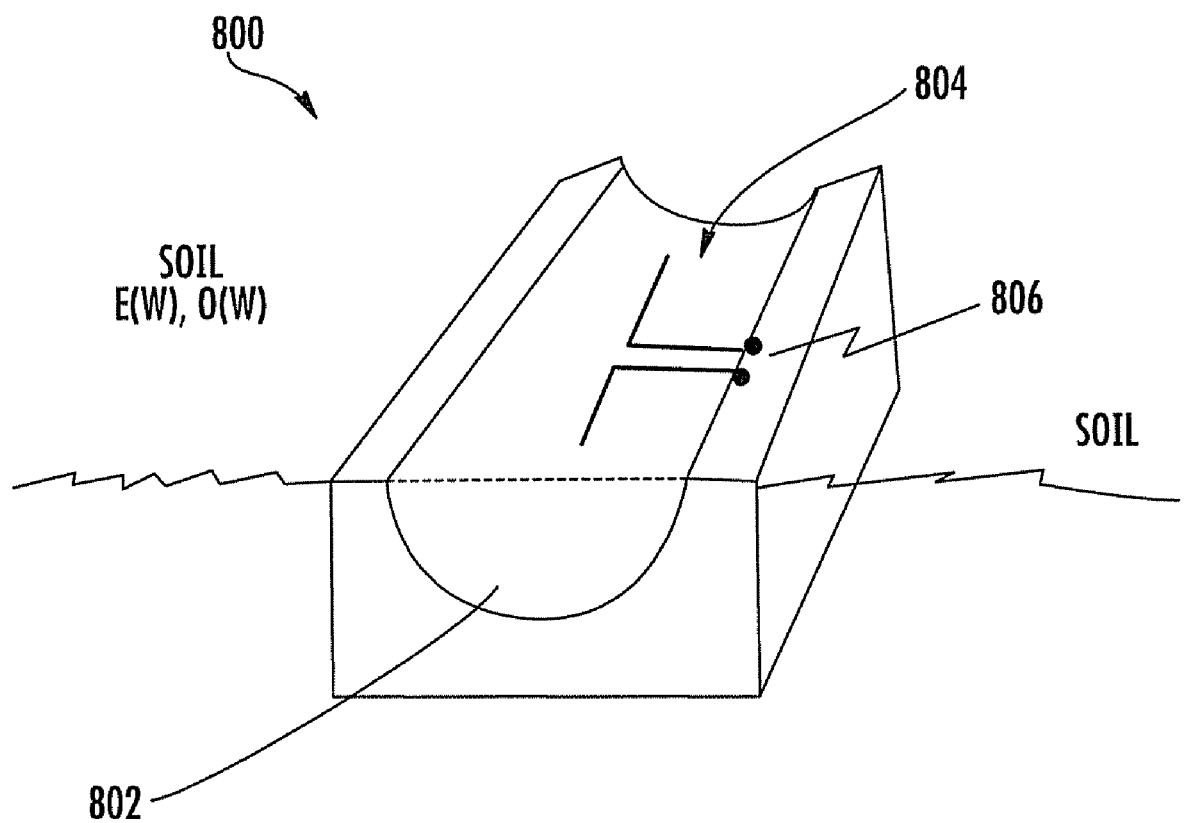
FIG. 8 is a top perspective view of a microwave moisture meter for use in material property gauges according to the subject matter described herein.

In one embodiment, a moisture property may be measured by operating a device to perform a frequency sweep on a microwave moisture meter (e.g., the meter shown in FIG. 8 and described herein). The moisture meter may operate in a self-impedance mode, wherein a complex terminal impedance is measured at the input of a dipole. In one example, the dipole resonates at 2.45 Ghz, at a resonance frequency where the return loss of the antenna is minimized. As water content increases, the dielectric constant of the sample material increases, and thus increases the electric field near field energy, thus reducing resonance.

Moisture measurement may rely on single variable or multi-variable equations. For example, water may be detected using one variable such as the relative dielectric constant $\in_r$. Interfacial polarization is an important property response for heterogeneous materials. Because of these polarization effects (also referred to as Maxwell-Wagner effects), a resonance is produced in the permittivity spectrum. This relaxation may be used for water content determination for a particular type of soil. At lower frequencies, the measured dielectric constant has the effects of the Maxwell-Wagner phenomenon, thus leading to errors in the water content measurement, which are also a function of temperature. Other exemplary variable include conductivity, permittivity, and the dispersion of the change in conductivity and the change of permittivity with frequency. Further, for example, the relaxation frequency of some soils is on the order of 27 Mhz. Further, the relaxation frequency of some soils is on the order of 10 MHz. Additional discussion is provided in U.S. patent application Ser. No. 10/971,546, filed Oct. 22, 2004 (U.S. Patent Application Publication No. 2005/015028), commonly assigned, and the disclosure of which is incorporated herein by reference in its entirety.

In one example, the capacitance of a fringing field detector is measured using a feedback loop in an oscillator circuit. The frequency is provided by the following equation (wherein $C_{eff}$ represents the effective capacitance including the surrounding medium, parasitics in the circuitry, and nominal capacitances in the tank circuit, and L represents the inductance):

$$2\pi F = 1/(\text{sqrt}(LC_{eff}))$$

The ratio between a reference frequency and the frequency with the fringing field capacitor switched in or included may be calibrated against moisture. The sensitivity of the measurement at these frequencies due to salt concentrations should be considered. The end result is that chemical composition errors must be corrected, leading to many different calibration curves for the soil types. Further, discussion is provided, for example, in U.S. Pat. Nos. 4,924,173; 4,929,885; and 5,260,666, each of which are incorporated herein by reference in their entireties.

Microwave-based moisture property detectors may be advantageous, for example, because such detectors can perform density-independent moisture measurements and are much less susceptible to chemical composition errors than their lower frequency counterparts. Such detectors may be advantageous over neutron-based moisture property detectors, because neutron-based detectors are density and material dependent. Further, it is desirable to reduce the use of neutron sources because of U.S. Nuclear Regulatory Commission (NRC) regulations and fees associated with neutron sources.

Gauge 100 may include a temperature sensor 142 operable to measure a temperature associated with construction material 106. Further, temperature 142 may be in communication with temperature circuitry 144 for producing an electrical signal representative of the measured temperature associated with construction material 106. Temperature sensor 142 may be positioned near or at a surface of construction material 106 when base plate 140 of gauge 100 is positioned on the surface of construction material 106 as shown in FIG. 1A. Exemplary temperature sensors include infrared heat sensors, optical infrared sensors, resistance temperature detectors (RTDs), thermocouples, solid state-based temperature sensors, and resistive-based temperature sensors.

PCB 130 may be operable to receive one or more of the electrical signals produced by PCB 128, 141, and temperature circuitry 144 for determining a property value associated with construction material 106. Further, PCB 130 may include an electromagnetic measurement manager 146 for receiving, managing, and processing electrical signals representative of electromagnetic fields. PCB 141 may be operable to communicate to manager 146 electrical signals representative of the detected electromagnetic fields. Manager 146 may include functionality for storing data related to the detected electromagnetic fields.

Another temperature sensor 147 may be positioned in a "downhole" configuration in the interior of penetrometer end 102. Temperature sensor 147 may be operable to measure a temperature associated with an interior of construction material 106 in a gauge transmission mode. An electrical signal representative of the measured temperature associated with the interior of construction material 106 may be communicated to PCB 130 for use in determining a property value associated with construction material 106.

An acoustical measurement manager 148 may be operable to receive, manage, and process electrical signals representative of acoustical energy. PCB 128 may be operable to communicate to manager 148 electrical signals representative of the detected acoustical energy. Manager 148 may include functionality for storing data related to the detected acoustical energy.

A temperature measurement manager 150 may be operable to receive, manage, and process electrical signals representative of temperature. Temperature circuitry 144 may be operable to communicate to manager 150 electrical signals representative of the detected temperatures. Manager 150 may include functionality for storing data related to the detected temperatures.

As described in further detail herein, a material property calculation function (MPC) 151 may receive data from managers 146, 148, and 150 regarding detected electromagnetic fields, acoustical energy, and temperatures associated with construction material 106. Further, MPC 151 may receive measurement data from sensor 143. The data may be used by MPC 151 for determining a property value of construction material 106. MPC 151 may include computer program instructions to determine the property value by using a portion or all of the data provided by managers 146, 148, and 150. For example, the data may be used for estimating a density of construction material 106 and/or correcting a density estimation of construction material 106. MPC 151 may be programmed with the equations and data described herein for estimating or determining the property value.

Further, MPC 151 may include suitable hardware, software, and/or firmware components for implementing measurement and calibration procedures according to the subject matter described herein. MPC 151 may include one or more processors and memory components. Exemplary MPC components include one or more of pre-amplifiers, spectroscopic grade Gaussian amplifiers, peak detectors, and analog-to-digital converters (ADCs) for performing the processes described herein. Procedure status, feedback, and density measurement information may be presented to an operator via one or more interfaces of gauge 100.

Gauge 100 may include an interface for receiving operator input and for displaying output to the operator. In particular, gauge 100 may include a display 152 for displaying output and a keypad 154 for receiving operator input. A calculated property value of construction material 106 may be displayed to an operator via display 152.

Figure 2A:
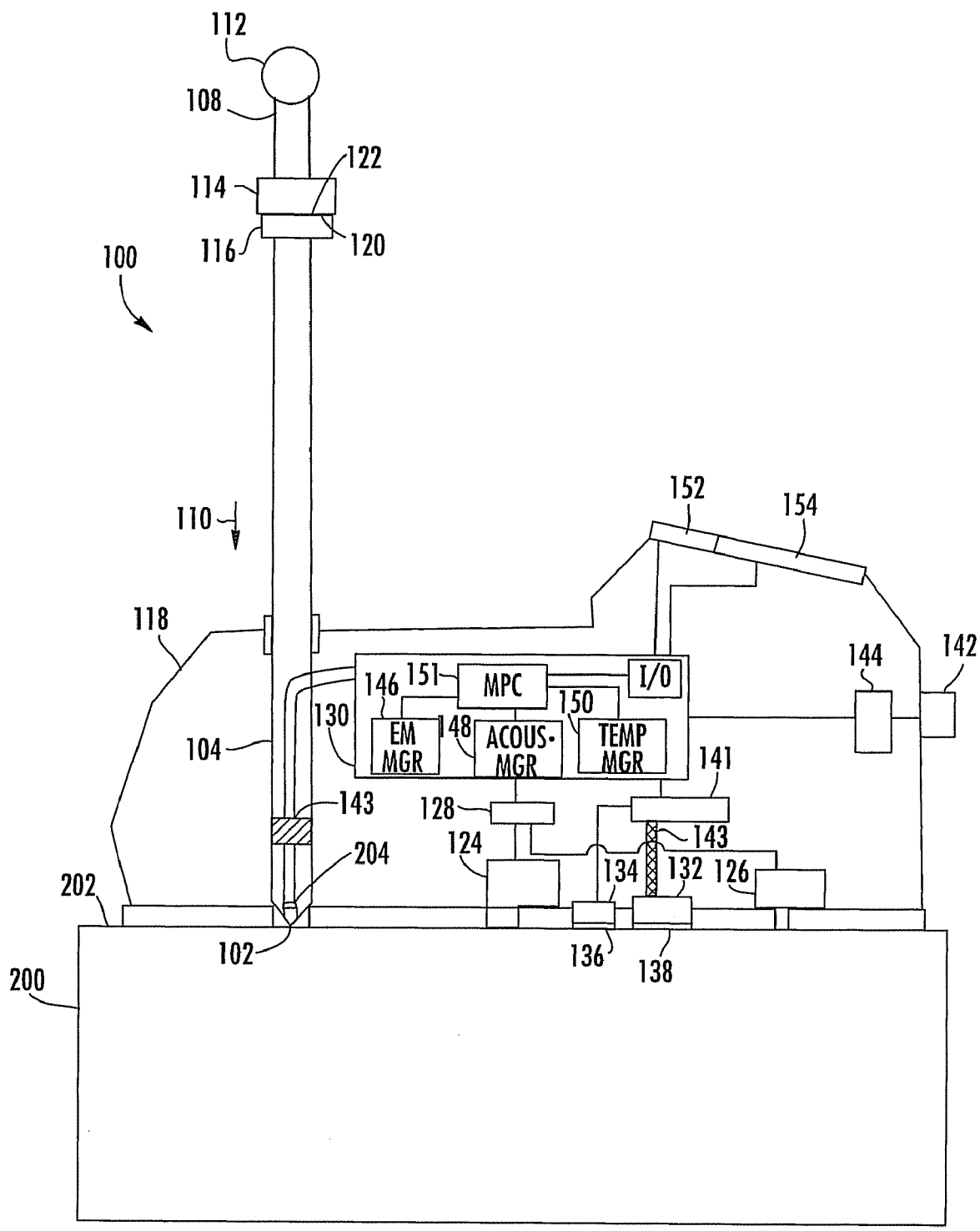
FIG. 2A is a vertical cross-sectional view of material property gauge shown in FIG. 1A configured in a backscatter mode for measuring the density or modulus of asphalt according to an embodiment of the subject matter described herein.

FIG. 2A is a vertical cross-sectional view of material property gauge 100 shown in FIG. 1A configured in a backscatter mode for measuring the density or modulus of asphalt 200 according to an embodiment of the subject matter described herein. Referring to FIG. 2A, in the backscatter mode, penetrometer 104 may be in a position that is raised with respect to the transmission mode such that end 102 is positioned on a surface 202 of asphalt 200. An accelerometer 204 may be positioned in the interior of end 102 for detecting acoustical energy from surface 202. Acoustical energy may be propagated to asphalt 200 by acoustical sources positioned on a surface, such as at the locations of acoustic detectors 124 and 126. The response of asphalt 200 to the acoustical energy may be detected by accelerometer 204 for analysis, the acoustical energy of which may be generated from a component internal to gauge 100 or another source. In another example, penetrometer 104 may, transmit acoustical energy into asphalt at end 102, and detected by accelerometer 204, acoustic detector 124, and/or acoustic detector 126 as the energy leaves end 102. Any of accelerometer 204 and acoustic detectors 124 and 126 may be used for triggering from detected acoustic energy generated by a component of gauge 100.

Further, accelerometer 204 may communicate an electrical signal representative of the acoustical energy to PCB 130 for processing and use in determining a property value associated with asphalt 200. For example, the data carried by the signal may be used for determining the density of asphalt 200. The data may be used alone or in combination with any of the other data detected by components of gauge 100. For example, the acoustical energy data may be combined with temperature measurements by temperature sensor 142 for determining a density or modulus of asphalt 200. In one example, penetrometer 104 is operable of exciting impulse or swept frequency waves into sample material 200 to be received by at least one of acoustic detectors 124 and 126. Modulus and density may be determined based on surface waves.

Figure 2B:
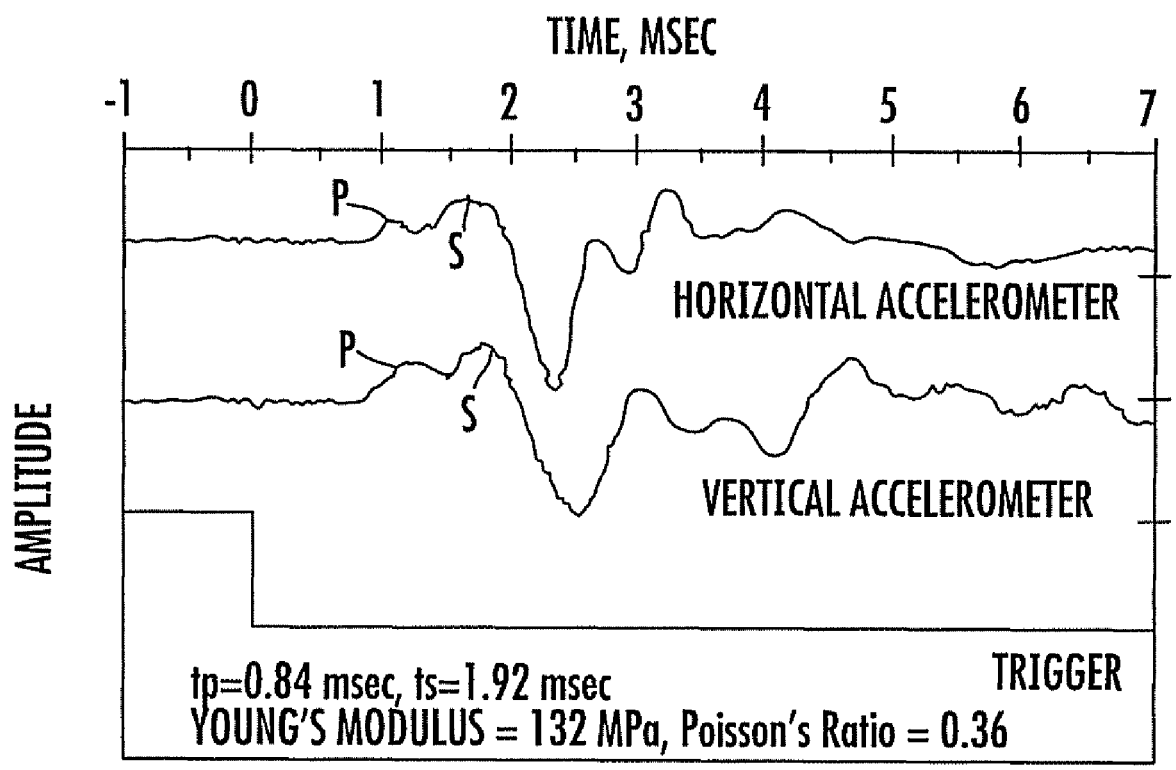
FIG. 2B is a graph of exemplary time domain waveforms as detected by accelerometer.

FIG. 2B is a graph illustrating exemplary time domain waveforms as detected by accelerometer 204. In this example, the acoustical energy is initiated at in the surface of a sample material by an impact at the locations of acoustic detectors 124 and 126. The two traces represent the X and Y directional sensors of triaxial accelerometer 204 in the horizontal and vertical directions, respectively. The acoustical energy propagates radially from the locations towards accelerometer 204 for detection. The wave indicated by P is detected by accelerometer 204 before the wave indicated by S.

Figure 2C:
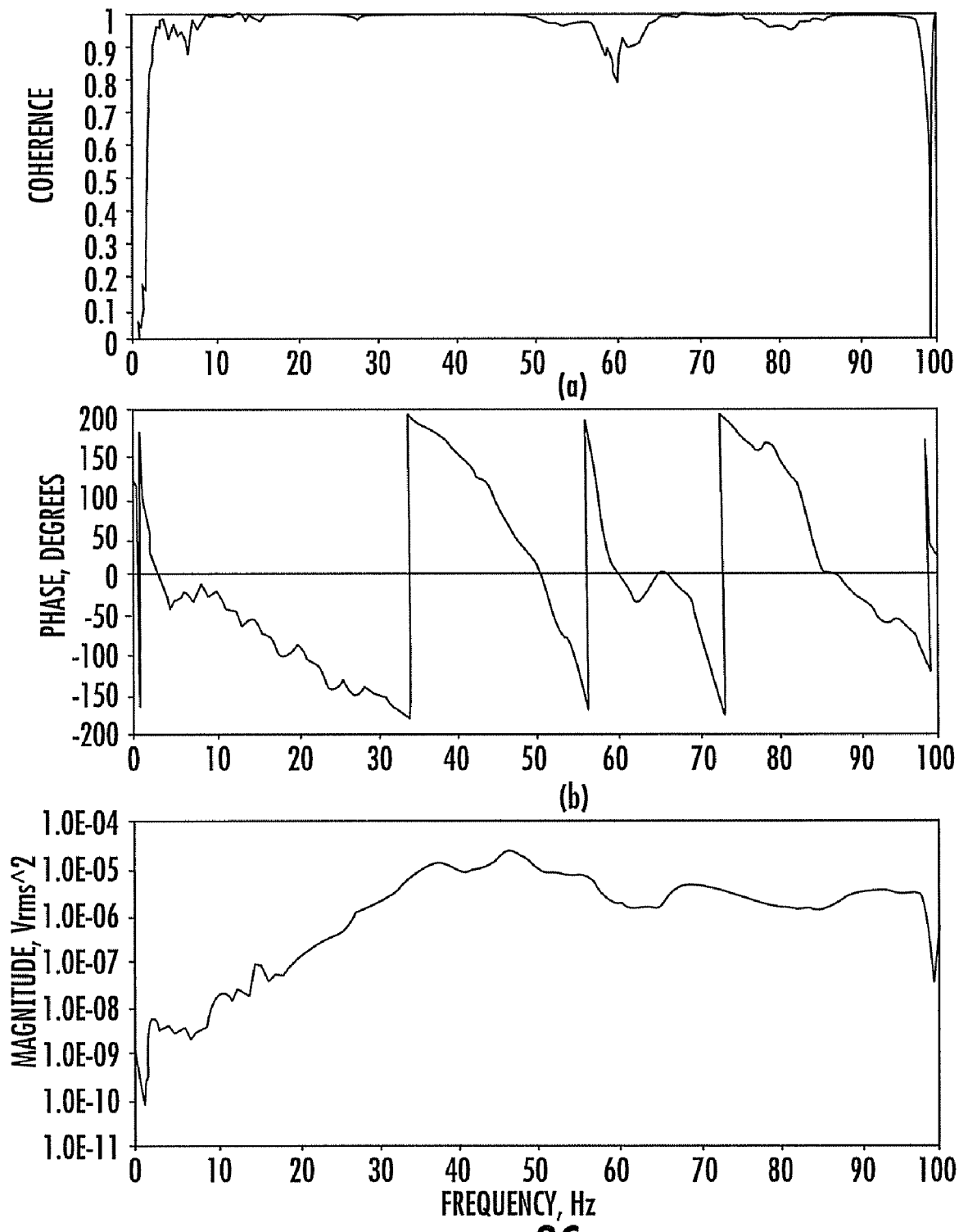
FIG. 2C is a graph of exemplary frequency domain signals with respect to coherence, phase, and magnitude.

FIG. 2C is a graph illustrating exemplary frequency domain signals with respect to coherence, phase, and magnitude. A coherence function may be used to obtain the quality of a signal. If the coherence is substantially less than 1, the measurement attempt is rejected. After about 5 good averages, the cross-power spectrum may be used to obtain phase and amplitude spectra.

An exemplary technique for the spectral analysis of surface waves (SASW) is described by Nazarian and Stoke in the publication "Nondestructive Evaluation of Pavement by Surface Wave Methods" (ASTM 1026, 1989), and "Nondestructive Testing of Concrete Structures Using the Rayleigh Wave Dispersion Method", by N. Krstulovic-Opara, R. Woods, N. Al-Shayea (AC Materials Journal, pp. 75-86, vol. 93, no. 1, 1996), and U.S. Pat. Nos. 5,614,670; and 5,095,465, the disclosures of which are incorporated herein by reference in their entireties. This technique measures the dispersive properties of the surface waves. By examining the phase velocity as a function of frequency or wavelength and using an inversion process, sample material properties as a function of thickness may be obtained. In use, the transfer and coherence functions between acoustic detectors may be determined. Further, the dispersion curve may be automatically assembled through the use of cross power spectrum and coherence functions. Analysis of the dispersion curve may yield the modulus of different layers of sample material.

Another exemplary technique similar to SASW is known as the ultrasonic surface wave method. In this technique, only a top layer of sample material is analyzed as the frequencies are much higher and wavelengths on the order of the surface thickness. As a result, complex numerical analysis for backcalculation of desired values is not necessary and the properties may be directly determined. The following equation may be used for determining shear modulus (where ρ represents mass density, v represents Poisson ratio, D represents the distance between acoustic detectors, and m represents the slope of the phase response in the transfer function between acoustic energy source and the acoustic detectors):

$$G = \rho[(1.13 - 0.16v)(m/D*360)]^2$$

In this approach, for operational modes of the gauges described herein, the Poisson ratio is either assumed or measured by the ratio of the P and S wave velocities. Further, the density may be determined or estimated according to the subject matter described herein. Alternatively, density may be determined by drill core sampling and laboratory testing based on Archimedes principles. An exemplary surface wave detector is described in U.S. Pat. No. 5,095,465, the disclosure of which is incorporated herein in its entirety. Time and frequency domain techniques may be used for calculating phase velocity, or for resonating acoustical waveguide structures with reflection and transmission analysis.

Figure 2D:
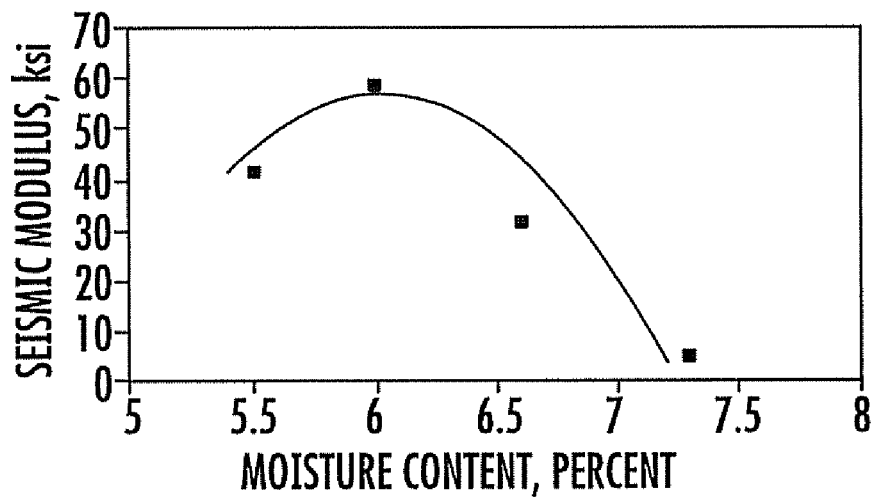
FIG. 2D is a graph showing a moisture-modulus curve.
Figure 2E:
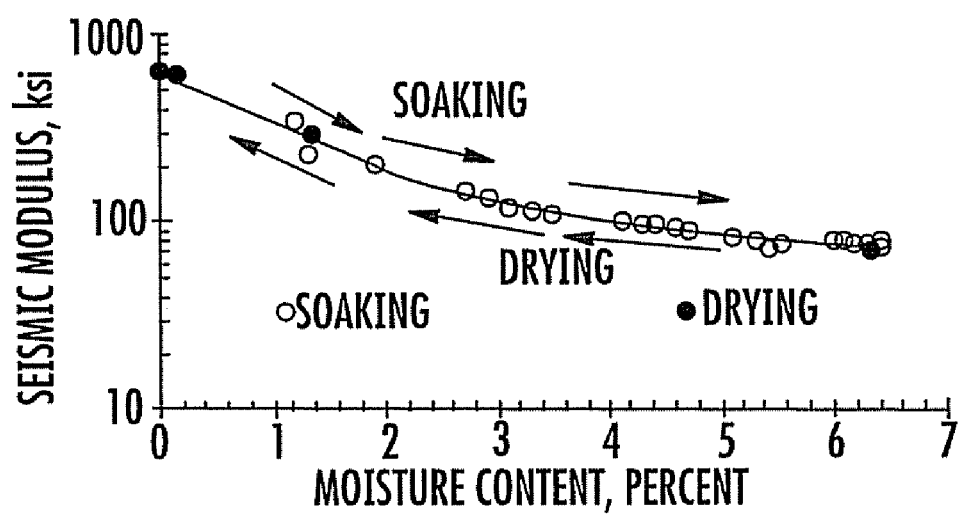
FIG. 2E is a graph showing modulus variations versus moisture content for the same sample material tested with respect to FIG. 2D.

Variations in moisture content of a sample material can significantly affect modulus. The material property gauges described herein may include functionality for correcting for moisture content variations in modulus calculations. For base construction materials such as soils, the modulus may be related to one of the construction parameters such as moisture. By performing a Proctor-like test, the optimum moisture-modulus curve may be obtained and are useful for calibration purposes. FIG. 2D is a graph showing a moisture-modulus curve. As shown in the graph, the optimum moisture content is about 6%. FIG. 2E is a graph showing modulus variations versus moisture content for the same sample material tested with respect to FIG. 2D. By fitting a polynomial function to this response and incorporating the fitted polynomial function into a field calibration, the field modulus of a sample material may be estimated as a function of moisture content.

In operational modes of the gauges described herein, dispersion may be determined by calculating phase velocity as a function of wavelength using the distance between acoustic detectors, or in the case of one acoustic detector, the distance between the acoustic source and the one acoustic detector. The following equation may be used for calculating the phase velocity (wherein f represents frequency, D represents the distance in meters, λ represents the wavelength in meters, and θ represents the phase in radians):

$$V_R(\lambda) = 2\pi f D/\theta$$

SASW or ultrasonic surface wave techniques may be integrated into the functionality of a material property measurement gauge as described herein. The equations may be programmed into an MPC and data obtained by gauge component detection for determining a property value of the sample material.

For flexible pavements, empirical models may be used for calculating the modulus of a sample material as a function of volumetric properties such as asphalt content, void ratio, binder viscosity, temperature, and mix design. For example, the following equation was determined by Witczak and reported in the publication "Typical Dynamic Moduli for North Carolina Asphalt Concrete Mixtures" by Y. R. Kim, M. Momen, and M. King (Final Report, FWHA/NC 2005-03):

$$\log|E^*| = -1.249937 + 0.029232 \cdot p_{200} - 0.001767 \cdot (p_{200})^2 - \\ 0.002841 \cdot p_4 - 0.058097 \cdot V_a - 0.80228 \cdot \frac{Vb_{\mathit{eff}}}{(Vb_{\mathit{eff}} + V_a)} + \\ \frac{3.871977 - 0.0021 \cdot p_4 + 0.003958 \cdot p_{38} - 0.000017 \cdot (p_{38})^2 + 0.005470 \cdot p_{34}}{1 + e^{(-0.603313 - 0.313351 \cdot \log(f) - 0.393532 \log(\eta))}}$$

where |E*|=the asphalt mix dynamic modulus in $10^5$ psi;
  η=bitumen viscosity in $10^6$ poise (at any temperature, degree of aging);
  f=load frequency in Hz;
  $V_a$=% air voids in the mix, by volume;
  $Vb_{\mathit{eff}}$=% effective bitumen content, by volume;
  $P_{34}$=% retained in the ¾ in. sieve, by total aggregate weight (cumulative);
  $P_{38}$=% retained in the ⅜ in. sieve, by total aggregate weight (cumulative);
  $P_4$=% retained in the No. 4 sieve, by total aggregate weight (cumulative); and
  $P_{200}$=% passing the No. 200 sieve, by total aggregate weight.

Further, the Hirsch model was developed for estimating the dynamic modulus of flexible pavement based on VMA, VFA, and binder modulus. The model is based on the law of mixtures for different phases of a material joined in series and parallel cells. The Hirsch model is represented by the following equation:

$$E^* = P_c \left[ 4200000(1 - VMA/100) + 3|G^*|\left(\frac{VFA \times VMA}{10000}\right) \right] + (1 - P_c)\left[\frac{1 - VMA/100}{4200000} + \frac{VMA}{3VFA|G^*|}\right]^{-1}$$

where $$P_c = \frac{\left(20 + \frac{VFA \times 3|G^*|}{VMA}\right)^{0.58}}{650 + \left(\frac{VFA \times 3|G^*|}{VMA}\right)^{0.58}} = \text{aggregate contact volume};$$

VFA=voids filled with asphalt,
VMA=voids in mineral aggregate; and
|G*|=dynamic shear modulus of binder.

By incorporating these models and equations into calculations performed by gauges according to the subject matter described herein, estimates of dynamic modulus may be obtained. Other suitable prediction models may be incorporated as well.

Figure 3:
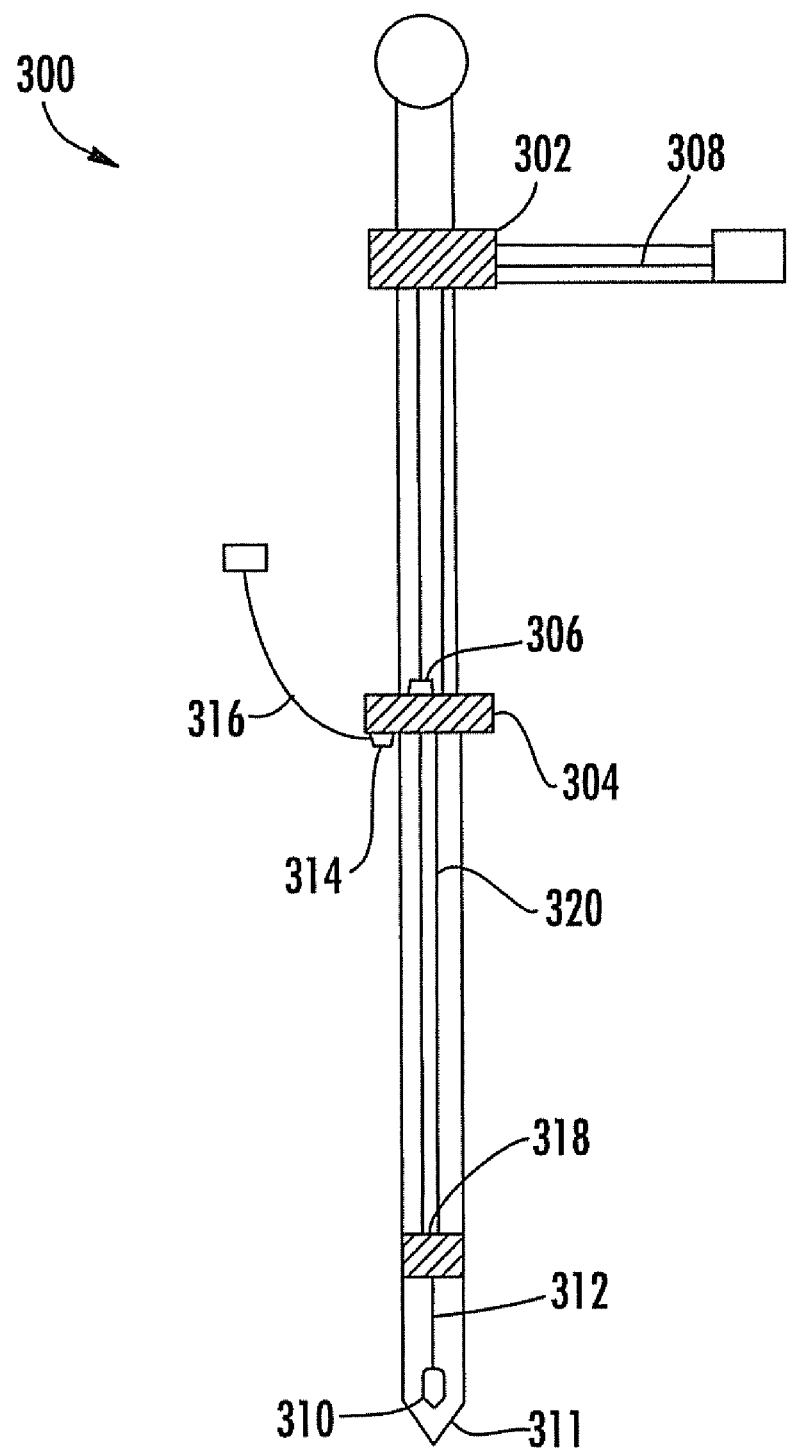
FIG. 3 is a vertical cross-sectional view of an instrumented dynamic cone penetrometer according to an embodiment of the subject matter described herein.

FIG. 3 illustrates a vertical cross-sectional view of an instrumented dynamic cone penetrometer (IDCP) 300 according to an embodiment of the subject matter described herein. Penetrometer 300 may be integrated into a gauge such as gauge 100 (shown in FIGS. 1 and 2). Data obtained by penetrometer 300 may be communicated to an MPC, such as MPC 151 shown in FIGS. 1 and 2), for use in determining a property value of a construction material. Referring to FIG. 3, penetrometer 300 may include a hammer component 302 and an anvil component 304 adapted for movement with respect to one another such that the components can impact with a force for producing acoustical energy into a construction material. Hammer component 302 may have a mass of about 1 kilogram. Penetrometer 300 may include a force transducer 306 operable to measure the contact force between components 302 and 304. An electrical signal representing the measured contact force may be communicated to the MPC via wire 308 for use in property value calculations.

Penetration resistance refers to the number of hammer impacts per millimeter. In one example, a force transducer may count the number of impacts, and the accelerometer may integrate to find the distance of penetration.

In another example, by storing data about the force and acceleration of an anvil, energy may be measured using the following equation:

$$E = \int F(t)V(t)dt$$

The distance or displacement of a tip end or cone end of a penetrometer into a construction material may be found by integrating the acceleration twice with respect to time. The soil resistance refers to the work done by the soil to stop the movement of the penetrometer tip end divided by the distance the penetrometer travels, which may be expressed using the following equation (wherein R represents the soil resistance, X represents the distance of travel with each impact of the hammer, and W represents the work equal to the change of kinetic energy=½ mV² with V being the final velocity striking the anvil to result from the earth's gravitational acceleration of 9.8 m/s²):

$$R = W/X$$

Further, penetrometer 300 may include a 3-axis accelerometer 310 positioned in the interior of penetrometer end 311, the end of penetrometer 300 for positioning in the interior of a sample material. Detectors 124 and 126 may be operable to detect acoustical energy from the sample material. The detected acoustical energy may be the acoustical energy propagated to the sample material from contact of components 302 and 304. Further, from surface excitations originating from detector 124 and/or detector 126, the response of the sample material to the acoustical energy may be detected by accelerometer 310. Further, accelerometer 310 may communicate an electrical signal representative of the acoustical energy to the MPC for processing and use in determining a property value associated with the sample material. The electrical signal may be communicated via a wire 312. For example, the data carried by the signal may be used for determining the density or stiffness depth profile of the sample material. The data may be used alone or in combination with any of the other data detected by components of the gauge. For example, the acoustical energy data may be combined with moisture measurements by a moisture sensor for determining a moisture corrected soil modulus. Similarly, when end 311 is positioned on the construction material surface and excites acoustic waves towards detectors 124 and 126, the acoustical energy data may be used with temperature measurements obtained by a temperature sensor for determining corrected asphalt modulus.

Penetrometer 300 may also include another accelerometer 314 attached to a bottom surface of anvil component 304. Accelerometer 314 may be operable to determine a velocity and sample material penetration distance by driving penetrometer 300 into the soil and storing the associated force and acceleration data. By twice integrating a signal obtained from accelerometer 314, the penetration distance may be determined. Further, accelerometer 314 may be operable to generate an electrical signal representing the determined velocity and sample material penetration distance and communicate the signal to the MPC via a wire 316 for use in calculating the penetration distance for each hammer impact. The resistance may be used to form a soil density profile as a function of depth, which may be used by an MPC for calculating a soil density or modulus.

A moisture sensor 318 may be positioned near end 311 of penetrometer 300 for placement in the interior of sample material. Moisture sensor 318 may be operable to measure moisture content of the sample material. An electrical signal representing the measured moisture content may be generated and communicated to the MPC via a wire 320. The measured moisture content may be used for determining a property value of the sample material. For example, the measured moisture content may be used to correct density measurements determined by other components of the gauge.

In one embodiment, multiple penetrometers may be used for obtaining acoustical measurements from different positions in the interior of a sample material. In one configuration, acoustical energy may be generated from the penetrometers. In another configuration, acoustical energy generated from a surface may be received at the ends of the penetrometers positioned in the sample material. The penetrometers may be coaxially aligned and parallel.

Penetrometers may be positioned in a sample material in any suitable manner such that the penetrating end of the penetrometer is tightly fitted to the sample material. For example, a drill rod technique may be used for positioning a penetrometer in a sample material. In another example, abrupt force may be applied to an end of penetrometer that is distal the sample material penetrating end for forcing the penetrometer into the sample material. An impact force may be applied, for example, by impacting an anvil component of the penetrometer with a hammer component. In this example, one or more accelerometers may be attached to the penetrometer for measuring the velocity of the penetrometer's movement and an impulse response of the sample material. This information may be used to determine a shear strength of the sample material simultaneously with the operation of the gauge. Other property values, such as density, of the sample material may be determined using the information. Similar techniques are described in the American Society of Testing and Materials (ASTM) standard D-4633 (known as the dynamic penetrometer test), the standard penetration test (SPT), and ASTM standards D-5778, D-3441, and D-6187.

The acoustic energy response of a sample material may be determined by examining the waves generated by the acoustic energy. In particular, for example, an impulse excitation may be applied to a penetrometer positioned in sample material as shown in FIG. 1A. Alternatively, impulse excitation may be applied to a top surface of the sample material. The impulse excitation may generate a disturbance in the sample material. Generally, the following two types of waves may be generated by the disturbance: P waves and S waves. P waves exhibit a push-pull motion to particles of the sample material, such as soil particles. S waves generate a motion that is transverse to the direction of propagation. The velocity of the P waves is higher than that of the S waves. Thus, the P waves arrive at an acoustic detector prior to the S waves.

The velocity of the waves may be found by dividing the distance between the source of excitation (or acoustical energy) and the acoustic detector by the time for arrival of the wave. In the deep interior of the sample material, body waves associated with the bulk modulus propagate. Table 1 below shows relationships between moduli and Poisson ratio (wherein Vp represents compressional wave velocity, and ρ represents mass density).

TABLE 1

Moduli and Poisson Ratio Relationships

| Bulk Modulus K | Young's Modulus E | Lames Constant $\lambda$ | Poisson Ratio $\mu$ | $\rho V_P^2$ | Sheer Modulus G |
|---|---|---|---|---|---|
| $\lambda + \dfrac{2G}{3}$ | $2\rho V_s^2(1+\mu)$ | $K - \dfrac{2}{3}G$ | $\dfrac{\lambda}{2(\lambda+G)}$ | $\lambda + 2\mu$ | $\dfrac{E}{2(1+\mu)}$ |
| $\dfrac{EG}{3(3G-E)}$ | $2\rho(1+\mu)(1.35-0.182\mu)^2 V_R^2$ | $G\dfrac{E-2G}{3G-E}$ | $\dfrac{3K-E}{6K}$ | $3K-2\lambda$ | $\dfrac{2}{3}(K-\lambda)$ |
| $\dfrac{E}{3(1-2\mu)}$ | $\dfrac{\rho V_P^2(1+\mu)(1-2\mu)}{1-\mu}$ | $\dfrac{2\mu G}{1-2\mu}$ | $\dfrac{3K-2\mu}{2(3K+\mu)}$ | $K + \dfrac{4}{3}\mu$ | $\lambda\dfrac{1-2\mu}{2\mu}$ |
| $G\dfrac{2(1+\mu)}{3(1-2\mu)}$ | $\dfrac{G(3\lambda+2G)}{\lambda+G}$ | $3K\dfrac{3K-E}{9K-E}$ | $\dfrac{E}{2\mu}-1$ | $\mu\dfrac{4\mu-E}{3\mu-E}$ | $3K\dfrac{1-2\mu}{2+2\mu}$ |
| $\lambda\dfrac{1+\mu}{3\mu}$ | $2G(1+\mu)$ | $3K\dfrac{\mu}{1+\mu}$ | $\dfrac{1}{2}\dfrac{\left(\dfrac{V_P}{V_S}\right)^2-2}{\left(\dfrac{V_P}{V_S}\right)^2-1}$ | $3K\dfrac{3K+E}{9K-E}$ | $\dfrac{3KE}{9K-E}$ |
| $\rho\left(V_P^2 - \dfrac{4}{3}V_S^2\right)$ | $3K(1-2\mu)$ | $\rho(V_P^2 - 2V_S^2)$ | | $\lambda\dfrac{1-\mu}{\mu}$ | $\rho V_s^2$ |
| | $\dfrac{9K\mu}{3K+\mu}$ | | | $\mu\dfrac{2-2\mu}{1-2\mu}$ | |
| | $9K\dfrac{K-\lambda}{3K-\lambda}$ | | | $3K\dfrac{1-\mu}{1+\mu}$ | |
| | $\lambda\dfrac{(1-\mu)(1-2\mu)}{\mu}$ | | | $\dfrac{E(1-\mu)}{(1+\mu)(1-2\mu)}$ | |

As stated above, the distance may be the distance between the tip end of a penetrometer and the acoustic detector. The arrival time may be determined for both wave types. Once the velocity is determined, the shear wave modulus may be calculated using the mass density ρ in the following equation:

$$G = \rho V_s^2$$

Alternatively, if the Poisson ratio v is known, the following equation relates Shear modulus to Young's modulus:

$$E = 2G(1+v) = 2\rho V_s^2(1+v)$$

In general, the Poisson ratio links the two types of wave velocities through the equation (where $\alpha = V_p/V_s$)

$$v = (0.5\alpha^2 - 1)/(\alpha^2 - 1)$$

Referring again to FIG. 2A, time domain traces from the two axes of an accelerometer are shown. When the source is horizontally close to the z-axis of the penetrometer, the waves travel predominantly vertical with compression-like characteristics. When the horizontal distance is increased, the horizontal accelerometer is predominant with shear energy. In one exemplary application, the maximum horizontal distance was 50 cm. Using signal processing and a programmed computer program product, the proper rise time for both P and S waves may be selected.

Other exemplary techniques for determining an impulse response of a sample material as a result of an impact are generally described by the publication "An Impact Testing Device for In-Situ Base Course Evaluation", by B. Clegg (ARRB Proceedings, vol. 8, pp. 1-6, 1976) and the ASTM standards D-5874-02, D-1883, D-5874, D-2216, D-4959, and D-4643, the disclosures of which are incorporated by reference herein in their entireties. A Clegg hammer is referred to a device operable to measure the impulse response of a soil halfspace as the result of a hammer impact. Further, for example, ASTM D-5874-02 describes a test method for determining the impact value (IV) of a soil. In the exemplary ASTM test method, a 4.5 kg mass is used for evaluating the strength of an unsaturated compacted fill for pavement materials, soils, soil-aggregates having a maximum particle size less than 37.5 mm. Further, lighter hammers of about 0.5 kg mass are applicable for lower strength soils such as fine grained cohesionless, highly organic, saturated or highly plastic soils having a particle size less than 9.5 mm. An accelerometer is attached to the hammer and peak of the response is recorded. The stiffer the soil, the less elastic it is, and the greater the de-acceleration. In use, the hammer is placed on the material either in the field or in a laboratory mold, raised to a fixed height and released. An average of four blows is typical of a single measurement. The impact value reflects and responds to changes in the soil characteristics influenced by strength. This is a dynamic penetration property similar to the California Bearing Ratio (CBR) test, the ASTM standard D-1883. According to ASTM standard D-5874, the method provides immediate results as a strength index value from which the quality of the fill may be inferred for the particular moisture conditions. This method also incorporates separate moisture measurements as described by, for example, ASTM standards D-2216, D-4959, and D-4643, wherein the water is removed by thermal methods and calculated as a percent of dry material. The peak acceleration can be integrated once for velocity as a function of time, and again for distance or penetration into the soil as a function of time.

Other exemplary techniques for determining the soil properties include cone penetrometer techniques. In a cone penetration test (CPT), a 60-degree apex cone at the end of a series of rods is pushed into the ground at a constant rate of 15-25 mm/s and continuous or intermittent measurements are made of the mechanical resistance to the penetration of the cone. A force is measured by means of a load cell just behind the cone. The force due to side friction is also measured directly above the cone using a sleeve in contact with the bore wall. Typical penetration cones have a diameter of 37.5 mm and an apex angle of 60 degrees. The total force Q as measured by strain gauges or other force sensors divided by the area A is the resistance q. The sleeve Force divided by the cylindrical sleeve area is the sleeve friction coefficient f. Cone penetrometers are use to investigate the subsurface geological strata, groundwater conditions, and the physical and mechanical properties of a soil or sub-base, and to classify the material. Because the diameter of the penetrometer can be on the order of 50 mm, and they are pushed into the soil at a constant rate, large rigs are normally used consisting of hydraulic jacking and reaction systems producing forces of 10-20 tons. Hence, these are not portable systems. Such miniature systems may be incorporated into the subject matter describe herein. The electrical parameters are inferred from measurements from the voltage at constant current across an electrode pair in contact with the soil. The formation factor F is defined as the ratio of the resistivity of the soil and the resistivity of the pore fluid. The formation factor F is linked to soil porosity n by the following equation (wherein A and m represent constants found in laboratory calibrations of field samples):

$$F=An^{-m}$$

Exemplary sensors that can be integrated into the CPT include
- Temperature
- Electrical resistivity
- Dielectric spectroscopy
- PH
- Redox Potential
- Gamma and Neutron sources/sensors
- Laser Induced Fluorescence
- IR or Optical cameras
- Liquid Samplers
- Vapor Samplers
- Moisture sensors
- Integrated Optics
- Ramon Spectroscopy
- Chemical Sensors
- MEMs
- Friction Sleeves
- Pore water quality
- Load cells All of theses sensors could be used to analyze a soil for contaminants, volumetric properties, mechanistic properties, moisture content, QC/QA of construction materials in general.

In one embodiment, a penetrometer may be a device that is positioned separate from a gauge housing. In one example, electrical signals generated by components of the penetrometer may be communicated to an MPC in the gauge housing by wires and/or wireless communication.

Figure 4:
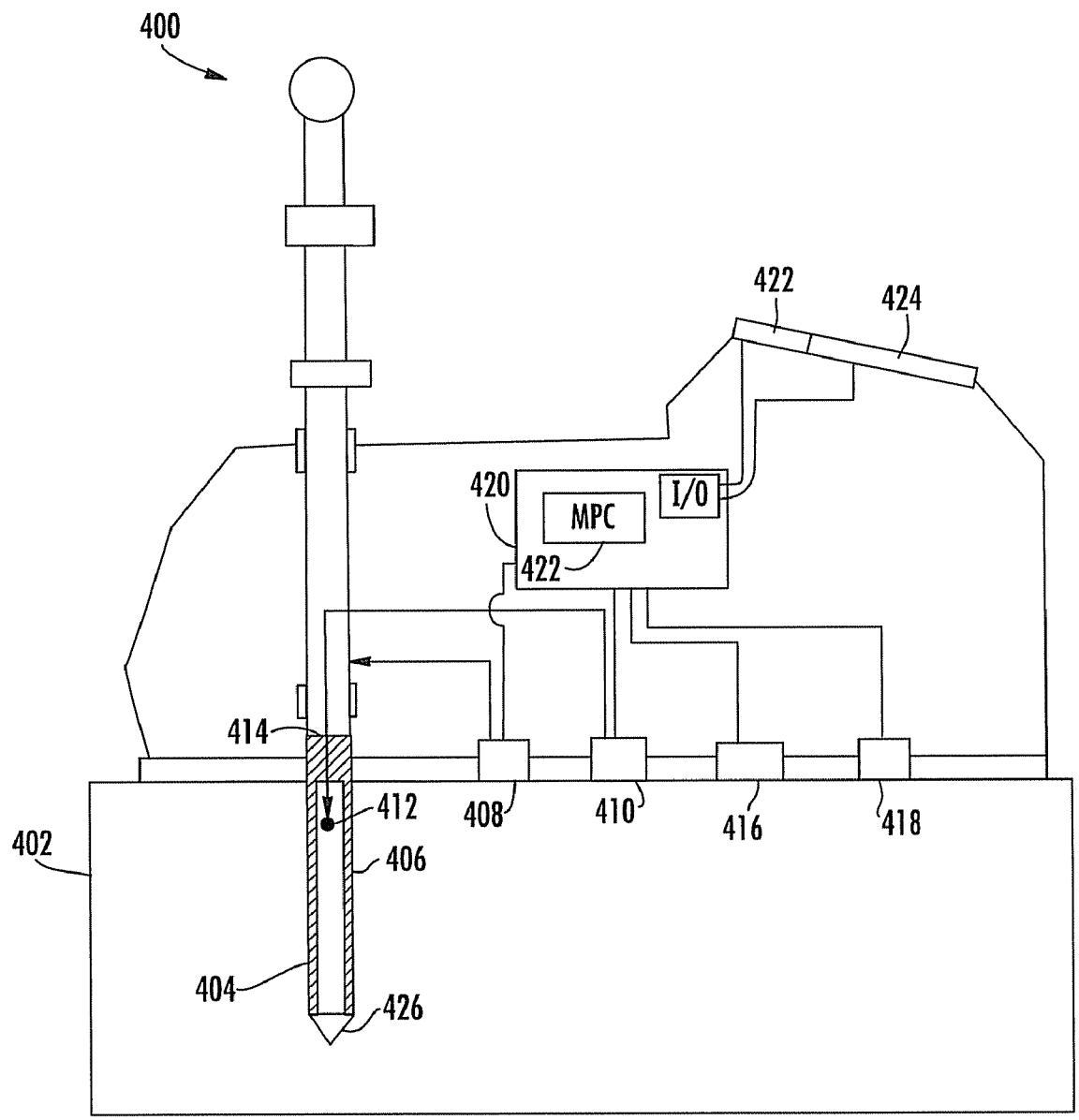
FIG. 4 is a vertical cross-sectional view of a material property gauge including a rod with electrical components integrated therein for use in measuring material sample properties according to an embodiment of the subject matter described herein.

According to one embodiment, a gauge penetrometer rod may be configured with electrical components for measuring electrical properties of a sample material. Exemplary sample material properties that may be measured include impedance, permittivity, permeability, and conductivity as a function of frequency. FIG. 4 is a vertical cross-sectional view of a material property gauge 400 including a rod with electrical components integrated therein for use in measuring material sample properties according to an embodiment of the subject matter described herein. Referring to FIG. 4, gauge 400 is operable to accurately determine a property value of a construction material 402. Gauge 400 may measure a property value of soil in a transmission mode and measure a property value of asphalt in a backscatter mode.

A rod 404 may include electrical components integrated therein for measuring electrical parameters associated with sample material 402. In particular, a conductive, exterior portion 406 of rod 404 may be coupled to electrical driving circuitry 408 operable to generate acoustical impulses (energy) and random signal sweeps into sample material 402. Further, a conductive component 410 may be coupled to electrical driving circuitry 412, which may be operable to generate ultra-wide electromagnetic microwave signals into sample material 402. Acoustic energy may be impulse excitations produced by an electric solenoid, a vibration shaker, a magnetostrictive device, bender elements, piezoelectric-based devices, or any device suitable to produce impulse or frequency domain signals. The electric signals may be defined by one or more oscillators. For a low band from about DC to about 30 Mhz, one or more phase-locked voltage controlled oscillators (VCOs) may be used for differing frequencies. A maximum frequency depends on the material under test. Further, an insulator 414 may be positioned in rod 404 for isolating acoustical and electrical measurements from the total length of rod 404 and for reducing the loss of high frequency measurements of currents in rod 404. As an alternative, time domain reflectometry (TDR) techniques may be used for generating acoustical impulses and electrical signaling.

Gauge 400 may include an electromagnetic sensor 416 for detecting sample material responses to electrical inputs from rod 404. For example, electromagnetic sensor 416 may be a wideband spiral antenna operable to detect sample material responses to electrical pulse signals generated by rod 404 and through time domain analysis. Further, for example, may be configured for measuring dielectric properties of sample material 402. Sensor 416 may be operable to generate an electrical signal representing the sample material responses to the electrical inputs.

An acoustic detector 418 may be operable to detect sample material responses to acoustical inputs from rod 404. Exemplary acoustic detectors include a geophone and a triaxial accelerometer. Alternatively, for example, acoustic detector 418 may include an impulse source for directing electromagnetic fields into sample material 402 and operable to detect sample material responses to the input. Detector 418 may be operable to generate an electrical signal representing the sample material responses to the acoustical inputs.

A PCB 420 may be operable to receive one or more of electrical signals produced by sensor 416 and detector 418 for use in determining property values associated with sample material 402. Further, PCB 420 may include a MPC 422 incorporating the data represented in the electrical signals for determining the property values. MPC 422 may include computer program instructions to determine the property values by using a portion or all of the data provided by sensor 416 and detector 418. For example, the data may be used for estimating a density of sample material 402 and/or correcting a density estimation of sample material 402. MPC 422 may be programmed with the equations and data described herein for estimating or determining the property value.

Further, MPC 422 may include suitable hardware, software, and/or firmware components for implementing measurement and calibration procedures according to the subject matter described herein. MPC 422 may include one or more processors and memory components. Exemplary MPC components include one or more of pre-amplifiers, spectroscopic grade Gaussian amplifiers, peak detectors, and analog-to-digital converters (ADCs) for performing the processes described herein. Procedure status, feedback, density, and modulus measurement information may be presented to an operator via one or more interfaces of gauge 100.

Gauge 400 may include an interface for receiving operator input and for displaying output to the operator. In particular, gauge 400 may include a display 422 for displaying output and a keypad 424 for receiving operator input. A calculated property value of sample material 402 may be displayed to an operator via display 422.

In one embodiment, gauge 400 may be positioned in a backscatter mode such that end 426 is on a surface of a sample material. In this mode, the generation of acoustical energy on the sample material surface may lead to the preferential excitement of particular wave types, such as Rayleigh waves, surface waves, shear waves, and/or compressional waves. Shear waves may also be generated by generating negative impulses. By adding the two waveforms together, the compressional components can be subtracted out for calculation purposes.

The data of the electromagnetic and acoustical sample material responses may be combined in calculations for determining a property value of sample material 402. The acoustical data is associated with yielding mechanical properties. The electromagnetic data is associated with yielding chemical properties, such as moisture content, clay content, mica content, cement content, etc. Further, the electromagnetic data may be correlated to mechanical properties, such as density. Calculations performed using acoustical data typically requires correction for density. Thus, electromagnetic and acoustical measurements may be used in accordance with the subject matter described herein to determine sample material properties, such as density and/or modulus.

Figure 5:
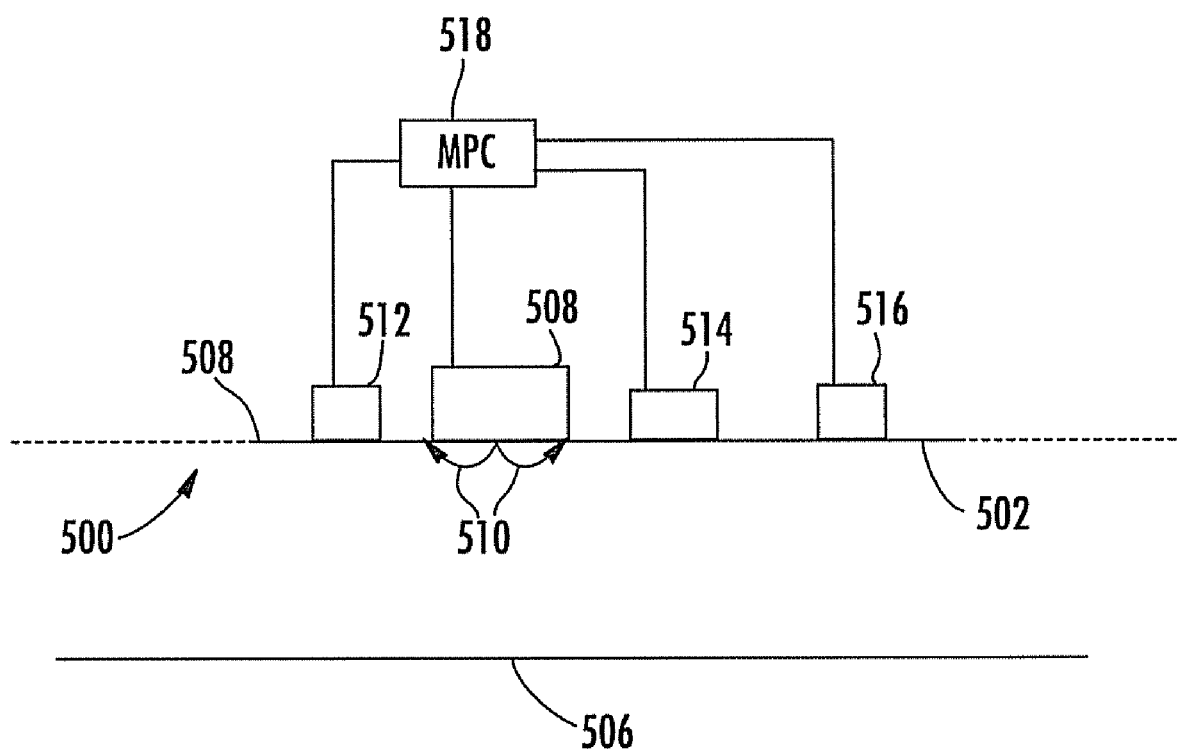
FIG. 5 is a partial vertical cross-sectional view of a portable seismic pavement analyzer (or material property gauge) including acoustic and electromagnetic components positioned on a bottom surface of the gauge according to an embodiment of the subject matter described herein.

Gauges may include acoustic and electromagnetic field components positioned on a bottom surface of the gauge for operation in a backscatter mode. FIG. 5 illustrates a partial vertical cross-sectional view of a portable seismic pavement analyzer (PSPA, DSPA) (or material property gauge) 500 including acoustic and electromagnetic components positioned on a bottom surface of the gauge according to an embodiment of the subject matter described herein. Referring to FIG. 5, gauge 500 may include a bottom surface 502 for positioning on a top surface 504 of sample material 506. An electromagnetic sensor/detector 508 operable to generate an electromagnetic field 510 and operable to detect a response to electromagnetic field 510 by sample material 506.

Further, gauge 500 may include an acoustic energy generator 512 operable to generate acoustic energy. Acoustic detectors 514 and 516 may be positioned in a spaced apart relationship with respect to one another and acoustic energy generator 512. Further, acoustic detectors 514 and 516 may be operable to detect a response to the generated acoustic energy by sample material 506.

An MPC 518 may be in communication with components 508, 512, 514, and 516 and operable to control the components and receive signaling representative of the response to the acoustic energy and electromagnetic field by sample material 506. The received signaling data may be utilized as described herein for determining one or more property values associated with sample material 506.

Figure 6:
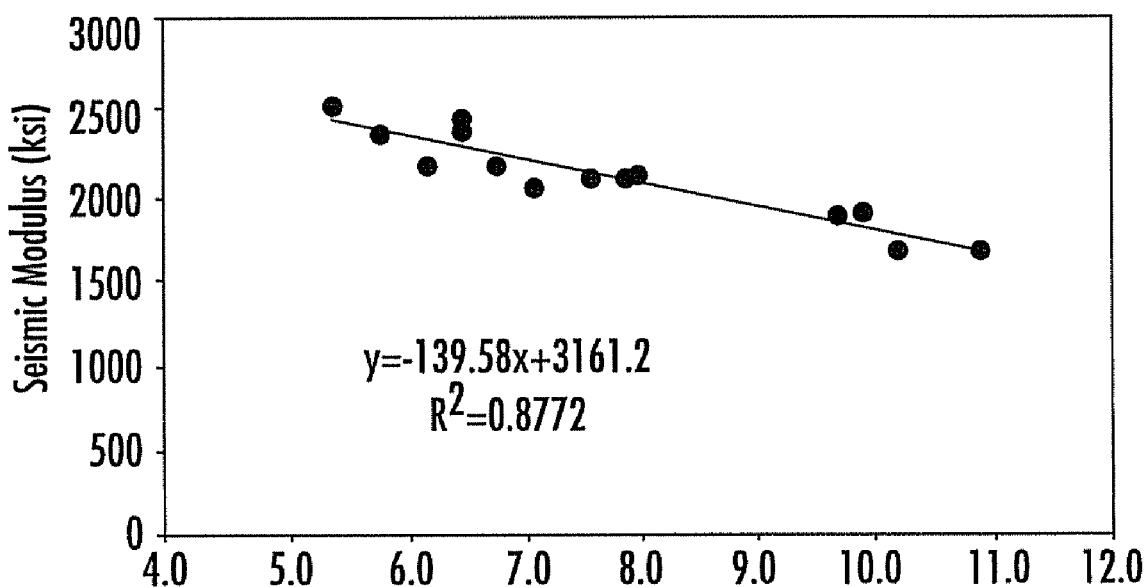
FIG. 6 is a graph showing the linear relationship between variations of a construction mix's void percentage and modulus.
Figure 7:
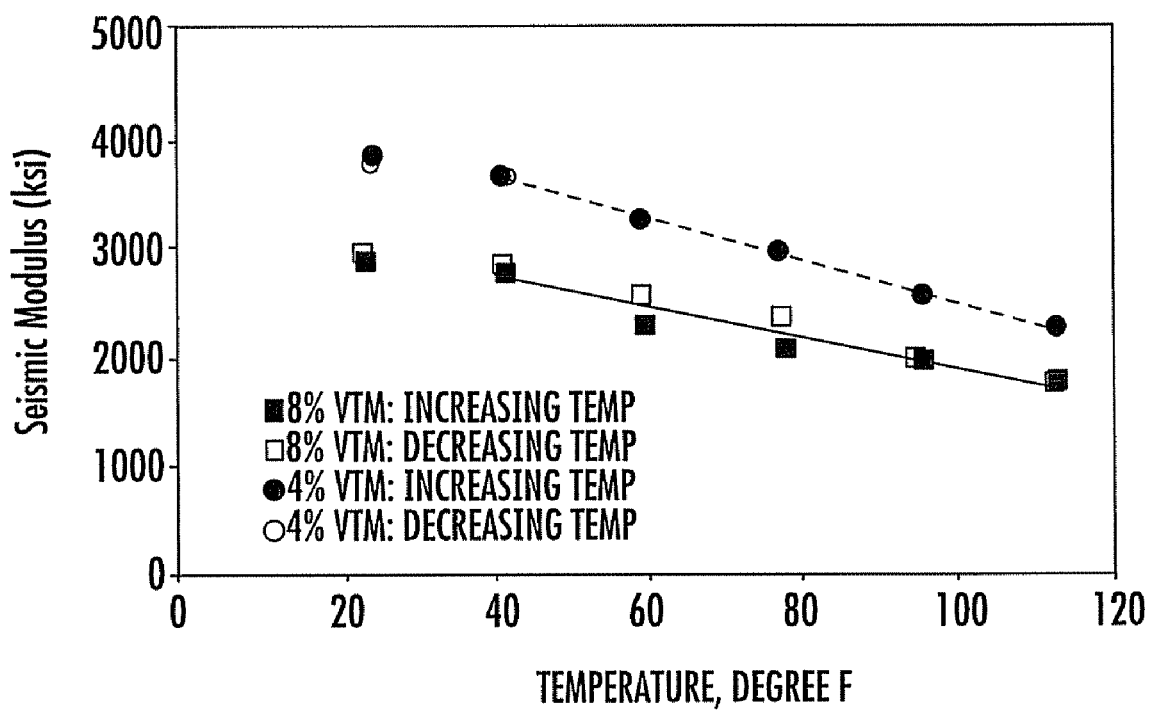
FIG. 7 is a graph showing the relationship between variations of asphalt temperature and modulus.

In one embodiment, void and temperature measurements may be made of sample material for use in density estimations and correcting density estimations. The total voids in a sample material is related to bulk density based on the maximum specific gravity (Gmm as described by ASTM standard D-2041 and AASHTO standard T-209). Modulus and void ratio are related in HMA. FIG. 6 is a graph showing the linear relationship between variations of a construction mix's void percentage and modulus. Further, the temperature of a sample material is related to bulk density (ASTM D-4311) and modulus. FIG. 7 is a graph showing the relationship between variations of asphalt temperature and modulus. The subject matter described herein may correct for density estimations using known relationships between void measurements and/or temperature measurements and modulus of a sample material. Further, correction for HMA modulus may be obtained by temperature correction. Thus, a method for non-nuclear density measurement may be implemented by the subject matter described herein. In as much as the acoustical phase velocity is related to the variables of sheer modulus G and mass density $\rho$, and electromagnetic methods are multi-variable and chaotic systems, the systems described herein yield accurate and repeatable density measurements.

Figure 9:
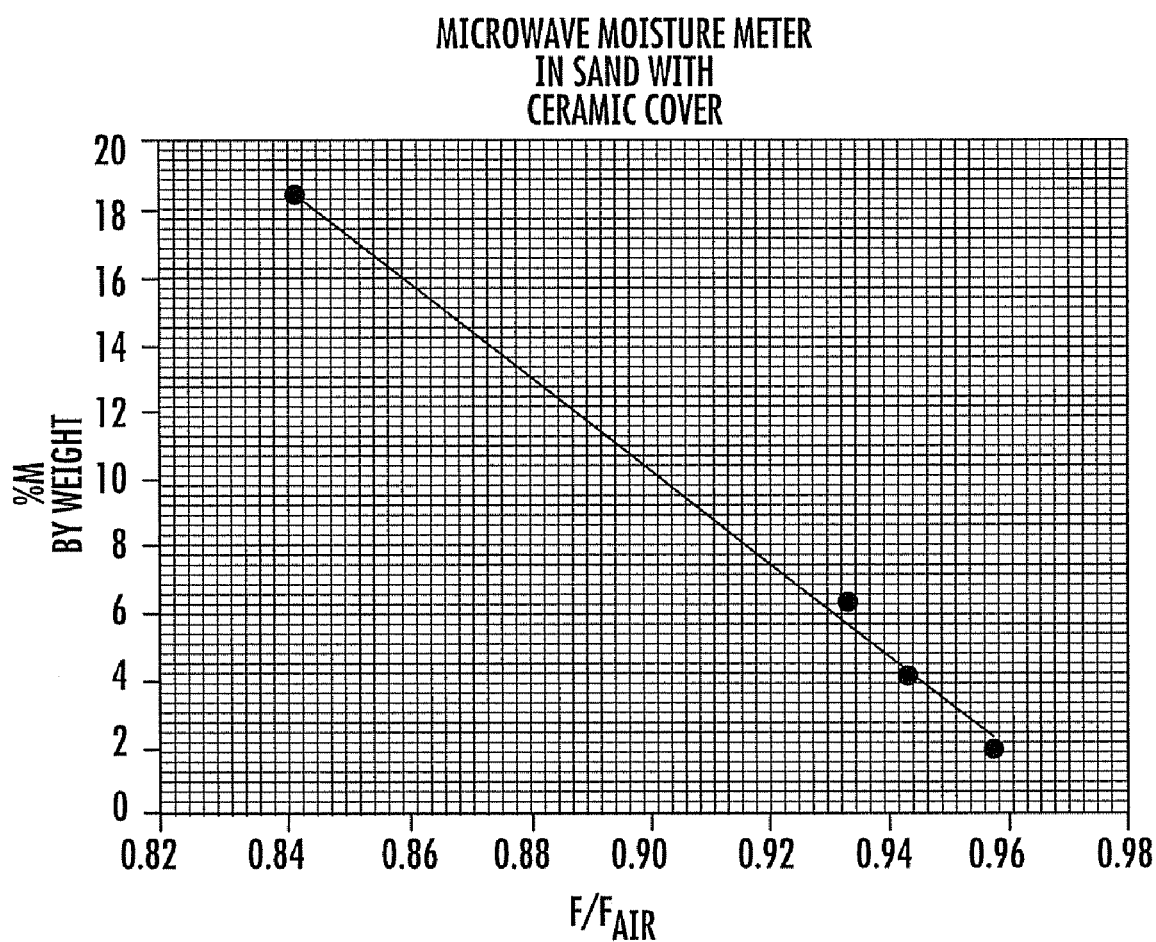
FIG. 9 is a graph showing frequency variations with respect to moisture content.

According to one embodiment, the material property gauges described herein may obtain moisture content measurements using a microwave moisture meter. The microwave band used by a microwave moisture meter may be less susceptible to ionic effects or errors associated with mineralogy of an aggregate or soil than other moisture measuring devices. FIG. 8 is a top perspective view of a microwave moisture meter 800 for use in material property gauges according to the subject matter described herein. Referring to FIG. 8, moisture meter 800 includes a metallic cavity filled with a high dielectric material 802. A 2.45 GHz dipole antenna 804 may be etched into a top surface of dielectric material 802. In one example, a ceramic cover may be positioned over antenna 804 for protection. The self-impedance of antenna 804 may be measured at terminals 806. In particular, the impedance as a function of frequency may be measured at terminals 806. In one example, the resonance of the cavity-backed antenna may be measured as a function of water content. FIG. 9 is a graph showing frequency variations with respect to moisture content.

In one embodiment, the permittivity of pavement construction material may be measured using lower frequency fringing or field coupling techniques.

Figure 10A:
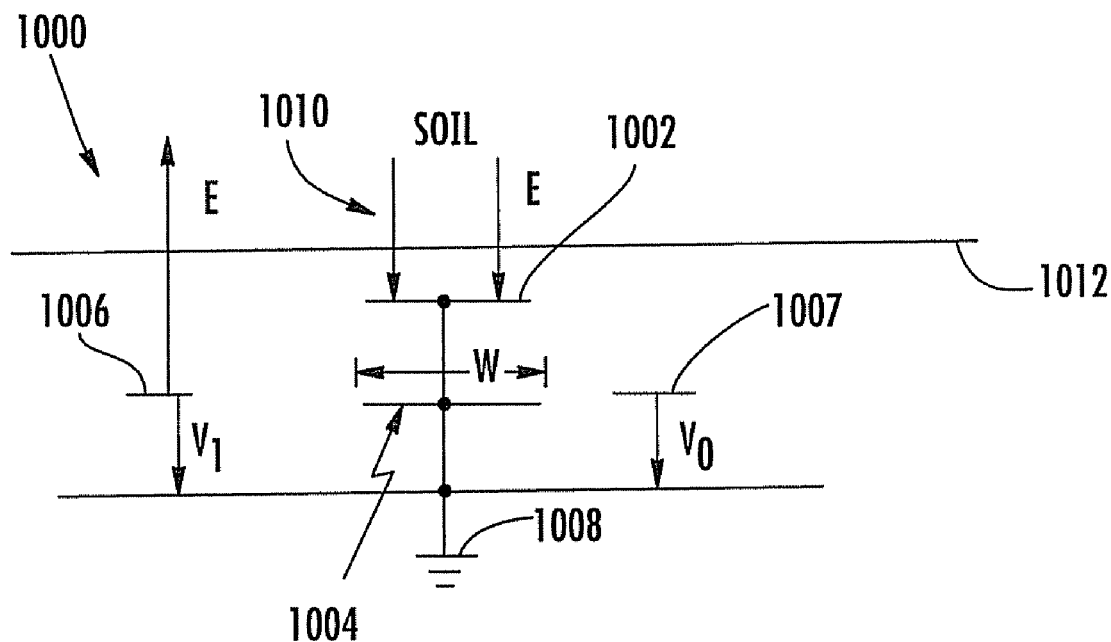
FIG. 10A is a vertical cross-sectional view of an exemplary lower frequency fringing sensor.

FIG. 10A is a vertical cross-sectional view of an exemplary lower frequency fringing sensor 1000. Sensor 1000 may be used as an electromagnetic sensor for detecting moisture in the gauges described herein. In this example, sensor 1000 is a strip or linear sensor. Sensor 1000 may also be used with gauges described herein to measure the void content of an asphalt mix. Referring to FIG. 10A, sensor 1000 may include conductors 1002, 1004, 1006, and 1007 and ground 1008. Conductor 1006 is operable as a source. Conductor 1007 is operable as a pickup. Each conductor level may be separated by an epoxy board or FR4, which is a printed circuit board material having a dielectric constant of about 4.2. Electric fields 1010 are emitted into soil 1012 and coupled back to conductor 1006. To a certain extent, as the frequency increases, the output voltage $V_0$ increases. This type of sensor may be particularly suitable for measurements in the UHF radio range. In particular, as the dielectric constant of soil 1012 (or asphalt in the alternative) increases, the output voltage $V_0$ increases proportionally. Capacitance techniques may be suitable for lower frequencies. Exemplary sensors are described in U.S. Pat. Nos. 6,400,161; 6,677,763; 6,803,771; 5,900,736; and U.S. Patent Application Publication No. 2003/0222662, the disclosures of which are incorporated herein by reference in their entireties. By utilizing a suitable integrated circuit, the amplitude and phase of a received signal may be digitized as a function of frequency, and the results analyzed for dispersion in the electromagnetic domain.

Figure 10B:
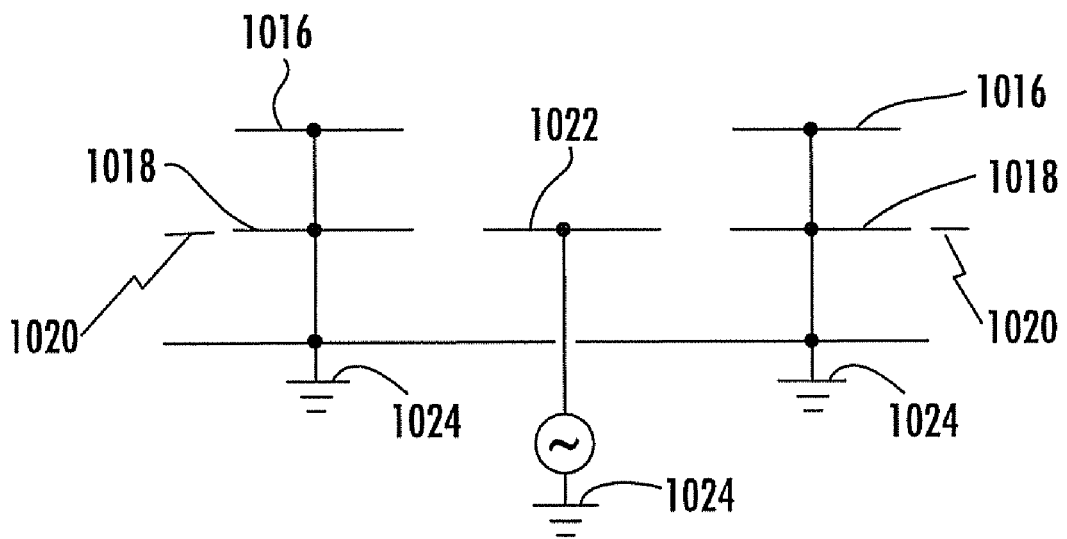
FIG. 10B is a vertical cross-sectional view of another exemplary lower frequency fringing sensor.

FIG. 10B is a vertical cross-sectional view of another exemplary lower frequency fringing sensor 1014. Referring to FIG. 10B, sensor 1014 is rotational symmetric such that a "ring shape" is formed by each of conductors 1016, 1018, and 1020. Conductor 1022 may form a disc-like shape. Further, conductor 1022 is operable as the source. Conductor 1018 is connected to ground 1024. During operation, fields may extend from conductor 1022 through a construction material and to conductor 1020. The voltage at conductor 1020 may be substantially less than the voltage applied at conductor 1022, but increases with the dielectric constant of the soil.

Sensors 1000 and 1014 shown in FIGS. 10A and 10B, respectively, may be formed in a variety of shapes. In particular, the sensors may be cylindrical, circular, or linearly-shaped. Further, the sensors may be symmetric about a central axis. Further, suitable shielding may be applied to the sensors for shielding stray or unintended fields.

Microwave-based moisture property detectors may be advantageous, for example, because such detectors are known to yield density-independent moisture measurements. Such detectors may be advantageous over neutron-based moisture property detectors, because neutron-based detectors are density and material dependent. Further, it is desirable to reduce the use of neutron sources because of NRC regulations and fees associated with neutron sources.

The moisture property detector components may be positioned in any suitable position in the interior or the exterior of a gauge. For example, a moisture signal source may be positioned in an end of a source rod for generating an electromagnetic field from within an interior of a sample material. In this example, a moisture signal detector may be positioned within a gauge housing for detecting the electromagnetic field transmitted through the sample material and generating a signal representing the detected electromagnetic field. Further, the generated electromagnetic field may be an electromagnetic pulse or step. In another example, a moisture signal source and detector may be attached to a drill rod operable to penetrate a sample material for positioning the moisture signal source in the interior of the sample material. In this example, the moisture signal detector may generate a signal representative of detected electromagnetic fields, and communicate the signal via a wired or wireless communication connection to an MPC in a gauge housing.

A moisture property detector according to the subject matter described herein may include one or more of several electromagnetic-based components. For example, the moisture property detector may include a duroid patch antenna configured to detect an electromagnetic field generated by an electromagnetic field source. The resonance frequency or input impedance may be monitored as a function of a dielectric constant. This moisture sensor operates in a self-impedance mode where the complex terminal impedance is measured at the input of the patch antenna feed. In this example, the patch may resonate at about 2.45 Ghz, where the return loss of the antenna is minimal and referred to as the resonance frequency. As the water content increases, the dielectric constant of the medium increases, and thus increases the electric near field energy, and lowers the resonance frequency.

Examples of this technique are described in U.S. Pat. No. 5,072,172, the disclosure of which is incorporated herein by reference in its entirety.

In another example, a moisture property detector may include a monopole. The monopole is broadband and may detect DC to microwave electromagnetic fields. In use, the monopole may be driven by an oscillator. The impedance may be measured as a function of frequency and various soil parameters obtained. Alternatively, the impulse response can be obtained and convolution and transform theory by be applied for obtaining soil properties. Further, the monopole may be coated by an insulator to reduce the energy loss in the soil.

During construction, the construction materials are typically exposed to an open air environment. Therefore, it is nearly impossible to control moisture content in most construction materials, especially road construction materials. Thus, wet densities are measured with the moisture content, and the dry density is calculated based on the wet density measurements. ASTM standards D-2922 and D-3017, incorporated herein by reference in their entireties, describe equations for dry density back calculations. Further, water affects the modulus of sample material. Therefore, for modulus and density measurements, correction is typically needed due to moisture.

Density-independent moisture measurements may be made based on a two-parameter measurement of attenuation (or magnitude) and phase shift in a transmission- or reflection-type mode. Alternatively, density-independent moisture measurements may be made using microwaves at a single frequency. A two-parameter method may be implemented by comparing the real and imaginary parts of the dielectric constant, as shown in the following equation (wherein $\in$ represents the dielectric constant):

$$\in = \in(\omega)' - j\in(\omega)''$$

A density independent calibration factor $A(\psi)$ (wherein $\psi$ is the wet-based volumetric water content) may be used for canceling density components. The principle of density-independent moisture measurements is based on both the real and imaginary part of the dielectric constant being related to dry material and water constituents, which change as a function of density. Density components may be empirically canceled by combining $\in(\rho_d, \psi)'$ and $j\in(\rho_d, \psi)''$ in the following equation:

$$A(\psi) = \frac{\varepsilon(\rho_d, \psi)' - 1}{\varepsilon(\rho_d, \psi)''}$$

The above equation assumes that $\in(\omega)'$ and $\in(\omega)''$ are linearly independent functions of $\rho_d$ and $\psi$.

The loss tangent $\in'/\in''$ may describe the material interaction and response. The behavior of the complex permittivity implies that normalizing both $\in(\omega)'$ and $j\in(\omega)''$ with density may reduce density effects. Further, data pairs may be normalized with bulk density as functions of temperature and moisture content. The following equation provides a measure of bulk density for particulate materials without prior knowledge of moisture content or temperature given that moisture density relationships are independent (wherein $a_f$ represents slope, k represents intercept, $a_f$ is related to the frequency, and k related to the dry dielectric):

$$\in''/\rho = a_f(\in'/\rho - k)$$

Alternatively, the following equation provides a measure of bulk density:

$$\rho = (a_f \in' - \in'')/ka_f$$

At high frequencies, water is the dominant factor associated with energy loss related to $\in''$ in the material, and the energy storage is related to $\in'$. Both are inversely related to density. Thus, a density-independent function for water content is based on the loss tangent $\in''/\in'$. Therefore, again, by normalizing the loss tangent by the density provided by the above equation results in the following equation:

$$\xi = \in''/(\in'(a_f \in' - \in''))$$

Here, the constant $ka_f$ is omitted, and the loss tangent has been normalized, resulting in a moisture function with reduced density effects. Experimentally, for granular materials, it has been found that $\sqrt{\xi}$ is linear with moisture content. $ka_f$ is a function of the measurement frequency and remains constant for data pairs of $\in'$ and $\in''$ when they have been normalized by density.

Based on experimental results, it can be shown that, as temperature increases, the bound water becomes easier to rotate and the dielectric constant increases. Thus, for the water measurement, temperature correction may be necessary.

Since $\xi$ is a function of moisture content with the density effects removed, and since it is experimentally found to be linearly related to moisture, calibration as a function of moisture and temperature can be implemented by fitting to the following linear equation (wherein $\xi$ represents a linear value in moisture M, and b represents a constant that is temperature dependent):

$$\sqrt{\xi} = A*M + B(T)$$

In this equation, the intercept B increases with temperature, but the slope A is constant. For granular materials, the following equation was empirically derived (wherein temperature is measured in Celsius):

$$B(T) = 9.77 \times 10^{-4} * T + 0.206$$

The moisture content may then be determined using the following equation:

$$\% M = (\sqrt{\xi}(a_f \in', \in'') - B(T))/A$$

In one embodiment, samples of soil may be extracted from the field and fit to this equation as a function of moisture yielding the constants A and B at a particular temperature. Generic curves may also be defined whereby a field offset is performed in use. Therefore, any moisture property detector operable to measure the real and/or imaginary portions of the dielectric constant of a material at a single frequency, multiple frequencies, or continuous sweeps of frequencies, chirps of frequency content, impulse responses and convolutions thereof, on the surface or down-hole can be incorporated into embodiments of the subject matter described herein.

Microwaves are more sensitive to free water than bound water but are also a function of the constituents of the chemical makeup of the dry mass and water mass mixture. However, a dry mass and water mass mixture is less susceptible to ionic motion and DC conductivity when considering the following equation:

$$\in = \in(\omega)' - j\in(\omega)'' = \in(\omega)' - j(\in(\omega)_d'' + \sigma_{d.c.}/\omega \in_0)$$

The higher frequencies reduce the effects of DC conductivity and measure more of the dielectric permittivity. However, soil specific calibrations may still be necessary. The differences in the calibrations are much smaller than their low frequency counterparts. Thus, if the material changes slightly without a gauge operator's knowledge, suitable results may still be obtained. Therefore, the microwave electromagnetic techniques have soil specific calibrations or offsets that may be required when comparing sandy loams to clay classes of soils.

As stated above, microwave measurements may be used for moisture measurements. In one example, a cavity-backed, microwave, dipole antenna may be used to measure the resonant frequency of sand of different moisture contents. Further, suitable techniques may be used to obtain material properties, such as moisture, porosity, clay content, and classification, using wideband microwave dispersion measurements.

When an electromagnetic field is applied to a lossy sample material, current flows and charge is rearranged on the sample material. As a result, a dipole-like electric field configuration on the sample material may be induced, and thus form a volume density of polarization P and free charge current density J. These volume densities are a result of constitutive parameters, dielectric constant $\in(\omega)$ and conductivity $\sigma(\omega)$. As soil material is non-homogeneous, the size of its particles, their relative geometry, orientation, and water content alter the response of electromagnetic waves in a complex manner. In general, for certain materials (e.g., clay), the sample material shows significant dispersion, e.g., as frequency $\omega$ increases, dielectric constant $\in$ decreases and conductivity $\sigma$ increases. The effect is reduced for high frequencies as compared to lower frequencies. Thus, sensors in the microwave range may be used for moisture measurements. Further, sweeping through low frequencies may result in a measurement of dispersion for use in classifying the sample material based on soil type.

In one example, soil content type and losses of sample material can be estimated by inspecting dielectric constant dispersion over a microwave bandwidth from DC to a few GHz. In particular, it has been shown that the type and amount of clay materials and the mineral-solution-interface characteristics may be determined using frequency dependent properties of the electrical impedance of the sample material. These electrical properties may be used in the measurement of soil porosity and strength, and used for classifying soil based on its sand/clay mixture. Further, these electrical properties may be used to calculate the modulus of a soil fabric. The acoustical and electromagnetic properties can be used to infer soil values such as porosity, water content, saturation, specific gravity of the soil solids, and nature of the stiffness of the tortuous soil skeleton, which in turn lead to values of density, modulus and stiffness.

Figure 11A:
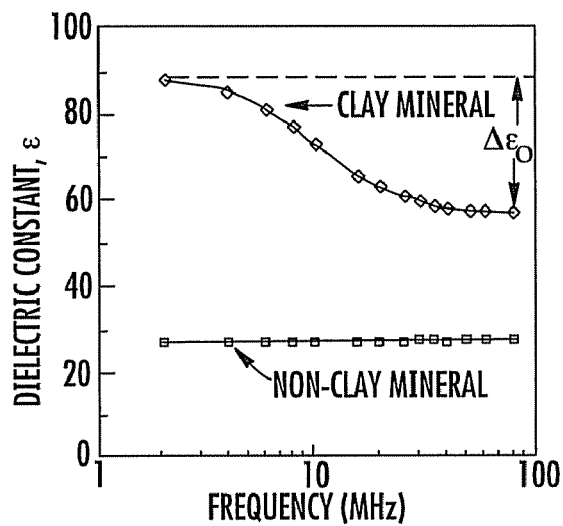
FIG. 11A is a graph showing a comparison of dielectric constants of clay material (cohesive soil) and non-clay material (non-cohesive soil) over different frequencies.

In summary, dielectric and acoustic properties including dispersion can address the following:
Soil classification cohesive vs. non-cohesive percents
Strength
Moisture content
Density
Porosity
Saturation
Specific gravity
Skeleton stiffness
Swelling
Corrosion
Organic/peat content In non-clay (sand) materials, the dielectric constant $\in$ and conductivity $\sigma$ response is independent of frequency. On the other hand, in hydrated clay materials, a relaxation occurs wherein these quantities change with frequency. FIG. 11A is a graph showing a comparison of dielectric constants of clay material (cohesive soil) and non-clay material (non-cohesive soil) over different frequencies.

Figure 11B:
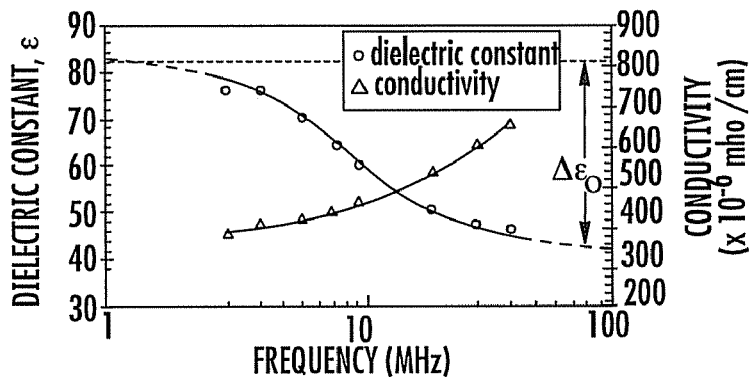
FIG. 11B is a graph showing the dielectric dispersion of the conductivity and dielectric constant of a cohesive soil.

FIG. 11B is a graph showing the dielectric dispersion of the conductivity and dielectric constant of a cohesive soil. It is noted that dielectric constant $\in(\omega)$ and conductivity $\sigma(\omega)$ are functions of frequency. The dielectric constant decreases and the conductivity increases with increased frequency.

Figure 11C:
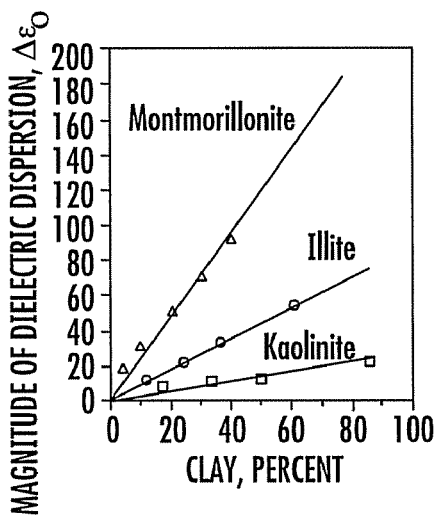
FIG. 11C is a graph showing dielectric constant dispersion of several different types of clays.

FIG. 11C is a graph showing dielectric constant dispersion of several different types of clays. Referring to FIG. 11C, it is apparent that different clays have different dispersion curves. Further, the dispersion depends on the mineralogy.

Information regarding dielectric constant dispersion for known materials may be used in the subject matter described herein for selecting calibration curves for radiation detectors and moisture property detectors. Further, the subject matter described herein may be a combination asphalt and soils gauge having operability to measure asphalt layers in a backscatter mode and soils in a transmission mode. Further, for example, a fringing field planar detector may be attached to a bottom surface of the gauge for simultaneously measuring electromagnetic density. In this mode, the nuclear component can calibrate the electromagnetic detectors in the field for improving the speed of access to a capacitance asphalt density indicator. Furthermore, by investigating the dielectric constant of a top depth (e.g., 1 cm depth) of material, an estimate of the surface roughness may be found for further nuclear density correction of rough surfaces. By comparing multiple sensors with different penetration depths less than about 1 cm, relative correction factors may be obtained.

An inhomogeneous sample material has a frequency dependent permittivity. In particular, a two-layer sample material may be modeled with the following equation (wherein $\in_{r\infty}$ represents a high frequency dielectric constant, $\in_{r\_s}$ is associated with the low frequencies, and $\tau$ represents the resonant time constant associated with a frequency $1/\tau$):

$$\in_r(\omega) = \in_{r\infty} + (\in_{r\_s} - \in_{r\infty})/(1+\omega^2\tau^2) - j\omega\tau(\in_{r\_s} - \in_{r\infty})/(1+\omega^2\tau^2)$$

This model may be used with soil classification techniques described herein for determining sample material properties, such as moisture content and density. Other dielectric dispersion techniques may be used for addressing soil classification cohesive/non-cohesive percentages, strength, moisture content, density, porosity, swelling, corrosion, and organic/peat content. Additional discussion is provided in U.S. patent application Ser. No. 10/971,546, filed Oct. 22, 2004 (U.S. Patent Application Publication No. 2005/015028), commonly assigned, and the disclosure of which is incorporated herein by reference in its entirety.

Figure 12:
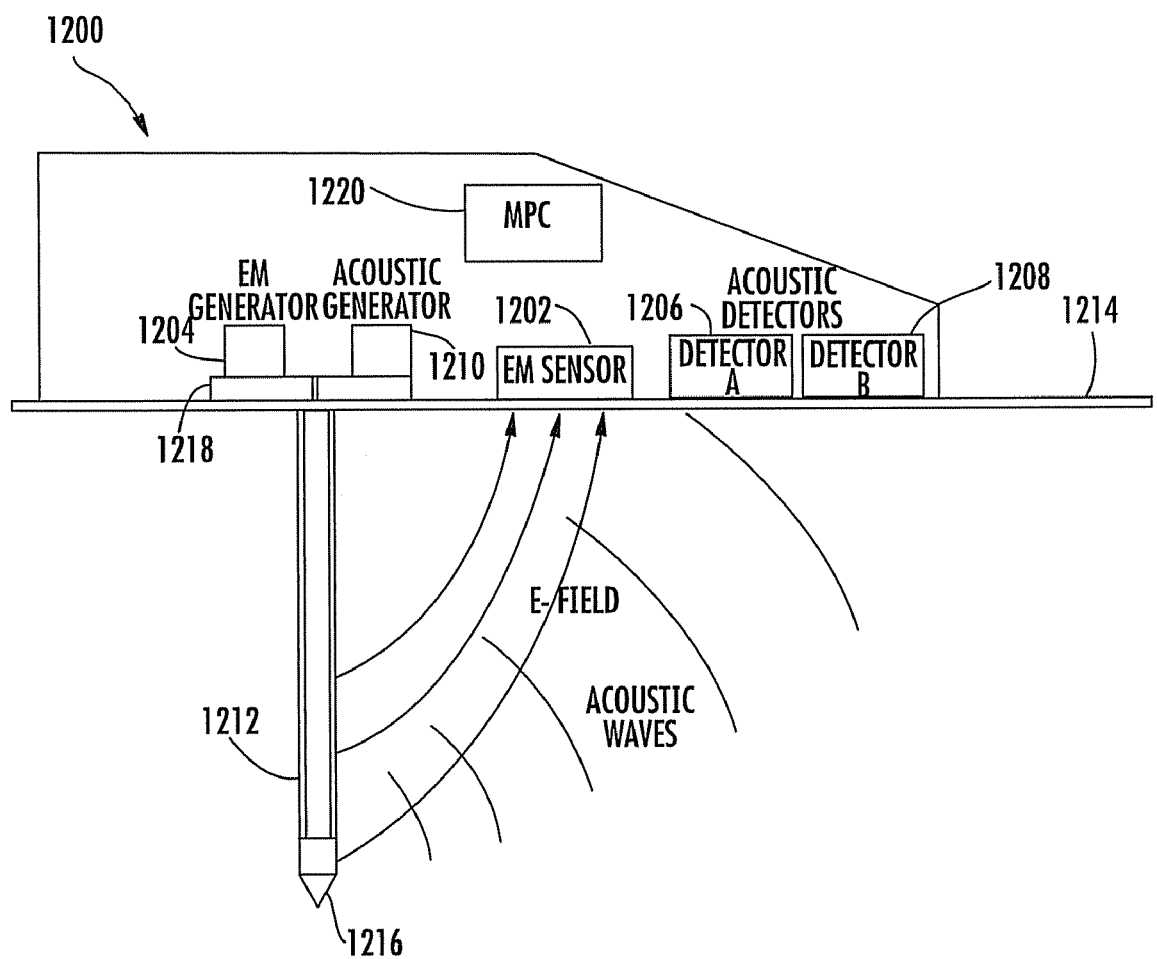
FIG. 12 is a schematic diagram of an exemplary material property gauge including acoustical impedance and electrical impedance functionality according to an embodiment of the subject matter described herein.

FIG. 12 illustrates a schematic diagram of an exemplary material property gauge 1200 including acoustical impedance and electrical impedance functionality according to an embodiment of the subject matter described herein. Referring to FIG. 12, gauge 1200 may include an electromagnetic field sensor 1202, an electromagnetic generator 1204, acoustic detectors 1206 and 1208, an acoustic generator 1210, and a penetrometer 1212. Gauge 1200 is operable to measure responses by construction material 1214 to an electromagnetic field and acoustical energy. Further, gauge 1200 may use the response data for determining one or more property values of construction material 1214, such as mechanistic values, volumetric values, and moisture content.

Penetrometer 1212 is a metal conductive rod having an insulative sheath on its exterior and a 60° cone tip 1216 for insertion into construction material 1214. Penetrometer 1212 may include components for use in measuring complex electrical parameters such as permittivity, permeability, and conductivity as a function of frequency. Electromagnetic generator 1204 and acoustic generator 1210 may be operably connected to penetrometer 1212 for emitting an electromagnetic field and acoustic energy waves from the interior of construction material 1214. The response of construction material 1214 to the emitted acoustic energy may be measured by acoustic detectors 1206 and 1208. The response of construction material 1214 to the emitted electromagnetic field may be measured by electromagnetic sensor 1202. In an alternative embodiment, penetrometer 1212 may be configured in a self-impedance mode as described herein for measuring impedance at driving point terminals.

In one example, penetrometer 1212 may function as a monopole. In this example, ground shielding may be provided by a conducting aluminum base 1218. Electromagnetic source 1204 may be swept from low frequency to resonance frequency, and the impedance of construction material 1214 obtained. Backcalculation may provide complex permittivity as a function of frequency, which is tabulated as the dielectric constant, conductivity, and the dispersive parameters, or the total decrease from low frequency to high frequency may be the changes in the dielectric constant or conductivity.

Calibrations may be stored in a memory of gauge 1200 for use in the field. When using a calibration routine, an offset may be required for moisture, density, or modulus measurements in field use. For asphalt, typical mixes include limestone and granite of several gradations and asphalt contents. For soils, several mixtures of clay and sand may be modeled into field selectable calibration routines, as described in more detail herein. The operator may have some prior knowledge of the construction material to be tested, and select a proper model based on the prior knowledge. Alternatively, the actual asphalt mix or soil from the base or sub-base of construction material may be physically characterized in a laboratory for moisture content, density, and modulus, and the data stored in a calibration routine for field use. Further, in the alternative, an adaptive and learning pattern recognition signal processes may be used for calibrating the gauge, such as a specialized algorithm, soft decision classification, basis shrinkage kernels, fuzzy logic, and neural networks. These processes may be used in a gauge according to the subject matter described herein for identifying and classifying soil type, for calculating moisture content, density, and modulus.

The insulative sheath on penetrometer 1212 may provide isolation between the acoustical measurements and the total length of penetrometer 1212. Further, the insulative sheath can function as an electrical insulator so that high frequency measurements have a reduced loss as the currents travel down the "monopole" of penetrometer 1212.

Acoustic detector 1206 may be a wideband spiral antenna that receives an electrical pulse signal from penetrometer 1212. By using time domain techniques, calculations may be performed using an MPC 1220 for determining average electrical parameters and for correlating the parameters to density and moisture content. Acoustic detector 1208 may be, for example, a geophone, triaxial accelerometer, or the like. In the alternative, acoustic detector 1208 may be replaced by an acoustic energy source for generating an acoustic impulse on the surface of material 1214 for detection and analysis.

The admittance of a probing antenna at low frequencies is known to be related to the electrical properties of the earth by the following equation (wherein $C_{air}$ represents the capacitance of the antenna in a dielectric medium of 1, and Y represents the admittance, i.e., the inverse of impedance):

$$Y = j\omega C_{air}(\in_r - \sigma/\omega\in_o)$$

For higher frequencies, the antenna may resonate and, generally, the impedance is provided by the following equation (wherein V represents the volume of integration, $Z_o$ represents the impedance of free space, E represents the vector field in the lossy medium, and E' is the vector electric field vector in free space):

$$Z_v = Z_o - (j\omega/I^2) \int (\in - \in_o) E \cdot E' dV$$

In use, a rational function of several coefficients may be used to describe the permittivity sensor, where calibration in at least 2 different mediums is required to determine the coefficients. Backcalculation of the admittance or impedance may yield the permittivity and conductance of the pavement material.

In one embodiment, a pulse or step of acoustic energy maybe applied to penetrometer 1212 for emission into construction material. The response of the construction material to the pulse or step may be measured by acoustic detector 1208 for analysis of travel time. The phase velocity and loss through the medium may be used, as described herein, to calculate the conductivity and dielectric constant of the material. Exemplary techniques for calibrations of different soils versus density are described by ASTM standard D-6780, the contents of which are disclosed by reference herein in its entirety.

In one embodiment, the gauge described herein may be configured with a radiation source and radiation detector for receiving a response to radiation by a sample material. The radiation response data may be used in combination with acoustic energy response data and/or electromagnetic field response data for determining a property of the sample material. For example, a density of a sample material may be estimated using radiation response data. In this example, acoustic energy response data and/or electromagnetic field response data may be used for correcting the density estimation based on the radiation response data.

Figure 13:
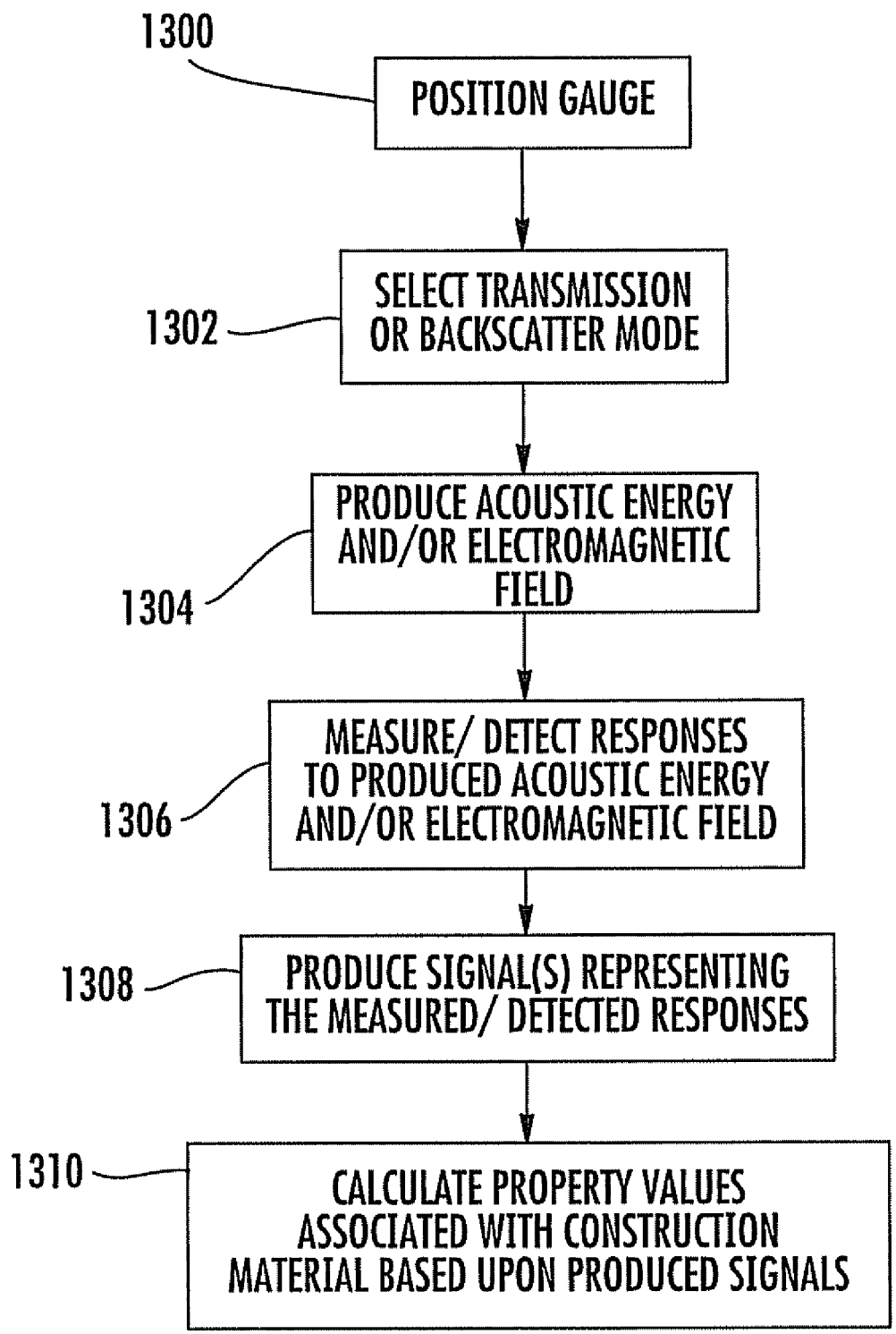
FIG. 13 is a flow chart of an exemplary process for property measurements using gauge shown in FIGS. 1A and 1B configured in a transmission mode or a backscatter mode according to an embodiment of the subject matter described herein.

As set forth above, a material property gauge according to the subject matter described herein may be utilized by an operator in a field and/or laboratory environment for obtaining property values of a sample material, such as a construction material. In particular, a material property gauge may be used for obtaining mechanistic, volumetric, and moisture content values associated with a construction material. Property value measurements may be determined using gauge 100 shown in FIGS. 1A and 2A configured in either a transmission mode or a backscatter mode. FIG. 13 is a flow chart illustrating an exemplary process for property measurements using gauge 100 configured in a transmission mode or a backscatter mode according to an embodiment of the subject matter described herein. Referring to FIG. 13, in block 1300, gauge 100 is positioned on a top surface of construction material 106 as shown in FIG. 1A in a transmission mode, wherein penetrometer 104 is lowered into an interior of construction material 106. Alternatively, gauge 100 is positioned on a top surface of construction material 106 as shown in FIG. 2A in a backscatter mode, wherein penetrometer 104 is raised such that tip end 102 is on a surface of construction material 106.

In block 1302, the operator may use display 152 and keypad 154 to select whether gauge 100 is configured in a transmission or backscatter mode. Based on the operator selection, the components of PCB 130 may be set for calculations in the selected mode.

In block 1304, based on the selected operational mode and the selected one of the transmission mode or the backscatter mode, the components of PCB 130 may activate acoustic sources and/or electromagnetic sources for producing acoustic energy and/or an electromagnetic field, respectively.

In block 1306, the components of PCB 130 may control the acoustic detectors and/or electromagnetic field sensors to measure/detect responses by construction material 106. Further, in one embodiment, temperature sensor 142 may be activated for sensing a temperature associated with construction material 106 for use in property value calculations. The measured/detected responses associated with construction material 106 may include P-wave seismic velocity ($V_p$), S-wave seismic velocity ($V_S$), K-bulk wave seismic velocity ($V_B$), dispersive real part of permittivity ($\in'(\omega)$), dispersive imaginary part of permittivity ($\in''(\omega)$), dispersive real part of conductivity ($\sigma'(\omega)$), dispersive imaginary part of permittivity ($\sigma'(\omega)$), Maxwell-Wagner relaxation time constant (T), temperature for corrections, instrumented dynamic cone penetrometer outputs (e.g., force, energy, acceleration, and moisture), total dielectric dispersion from low to high frequencies above Maxwell-Wagner effects ($\Delta\in$), and total conductance dispersion from low to high frequencies above Maxwell-Wagner effects ($\Delta\sigma$). These exemplary values may be referred to as constitutive parameters in electromagnetics and acoustics.

In block 1308, signals may be produced by acoustic detectors, electromagnetic field sensors, and/or the temperature sensor representing the measured and/or detected responses by construction material 106. The signals may be communicated to MPC 151 for use in calculating the property values.

In block 1310, MPC 151 may calculate one or more property values associated with construction material 106 based upon the produced signals. MPC 151 may apply the data in the signals to one or more of the equations described herein for estimating property values and/or correcting property value estimations. An operator may select whether a stored process in MPC 151 is to determine classification of material, and therefore select calibration coefficients. In particular, the operator may select to either of the following: (1) MPC 151 provide calibration coefficients; (2) the operator selects material type and calibration curves; and (3) a generic calibration that shows increases or decreases in relative values. After the type of calibration is selected, pattern recognition signal processing algorithms may be used to calculate property values, such as moisture, density, and modulus.

In block 1312, the calculated property values may be displayed to the operator. For example, the property values may be displayed via display 152.

Figure 14:
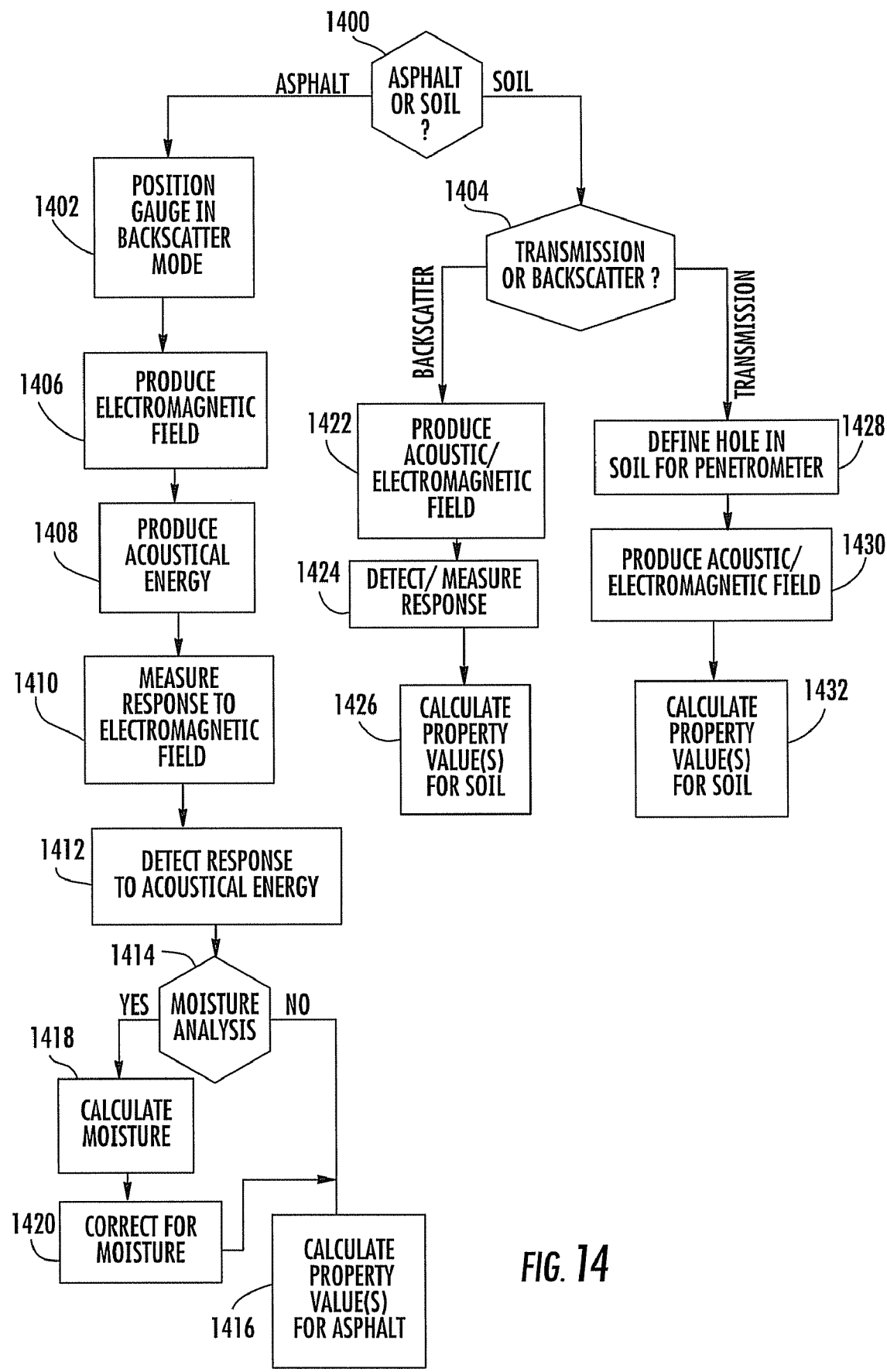
FIG. 14 is a flow chart illustrating an exemplary process for property measurements using gauge shown in FIGS. 1A and 1B for surface analysis according to an embodiment of the subject matter described herein.

As stated above, a material property gauge in accordance with the subject matter described herein may be used for surface analysis of a construction material. FIG. 14 is a flow chart illustrating an exemplary process for property measurements using gauge 100 for surface analysis according to an embodiment of the subject matter described herein. Referring to FIG. 14, in block 1400, the operator may determine whether to use gauge 100 for property value measurements of asphalt or soil. If asphalt is determined, the operator may position gauge in the backscatter mode (block 1402). Otherwise, if soil is determined, the process proceeds to block 1404.

In block 1406, gauge 100 may produce an electromagnetic field. Further, in block 1408, gauge 100 may produce acoustical energy. The response of the construction material to the electromagnetic field may be measured by electromagnetic sensor 132 of gauge 100 (block 1410). Further, the response of the construction material to the acoustical energy may be detected by acoustic detectors 124 and 126 (block 1412).

In block 1414, gauge 100 may determine whether to conduct moisture analysis for use in correcting property value determinations, such as density or modulus. In one example, the operator may select to conduct moisture analysis.

In another example, MPC 151 may determine whether to conduct moisture analysis. If it is determined not to conduct moisture analysis, one or more property values may be determined for the asphalt without the use of moisture value corrections (block 1416).

If it is determined to conduct moisture analysis, moisture values may be calculated (block 1418) and applied for correcting for moisture (block 1420). The moisture value calculations may be used in block 1416 for calculating one or more property values for asphalt (block 1416).

For measuring soil, in block 1404, the operator may select to configure gauge 100 in a transmission mode or a backscatter mode and manually configure gauge 100 for operation in the selected mode. If backscatter mode is selected, gauge 100 may produce an electromagnetic field and acoustical energy into the soil (block 1422). The response of the construction material to the electromagnetic field and the acoustical energy may be detected by gauge 100 (block 1424). Next, calculations for property values of the soil may be calculated based on the response (block 1426).

If the transmission mode is selected in block 1404, a depth for penetrometer 104 may be selected and a hole of suitable depth defined in the soil. The penetrometer may be placed in the hole in the transmission mode configuration. Gauge 100 may produce an electromagnetic field and acoustical energy into the soil (block 1430). The response of the construction material to the electromagnetic field and the acoustical energy may be detected by gauge 100 (block 1432). Next, calculations for property values of the soil may be calculated based on the response (block 1434). Instrumented penetrometers can obtain information about the soil strata for example soil strength (density, modulus) as a function of depth, which can be included in the data storage for signal processing. This information can aid the final analysis of the state of the soil.

Figure 15:
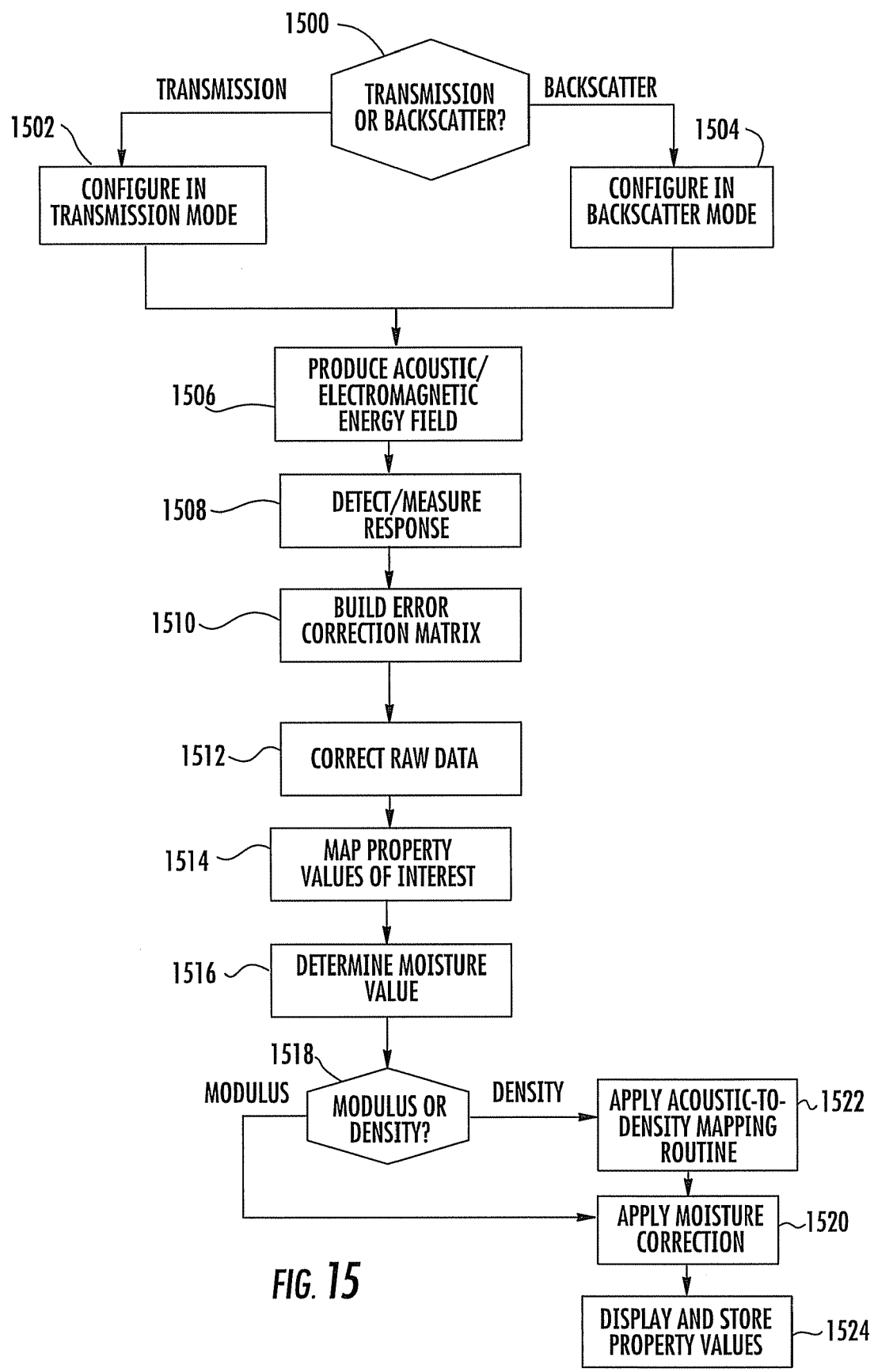
FIG. 15 is a flow chart of an exemplary process for measuring soil modulus according to an embodiment of the subject matter described herein.

FIG. 15 is a flow chart illustrating an exemplary process for measuring soil modulus according to an embodiment of the subject matter described herein. Gauge 100 shown in FIGS. 1A and 2A is referenced in this exemplary process. Referring to FIG. 15, in block 1500, the operator may select to configure gauge 100 in a transmission mode or a backscatter mode. If a transmission mode is selected, the operator may configure gauge 100 in the transmission mode as shown in FIG. 1A. (block 1502). If a backscatter mode is selected, the operator may configure gauge 100 in the backscatter mod as shown in FIG. 2A (block 1504).

In block 1506, gauge 100 may produce an electromagnetic field and acoustical energy into the soil. The response of the soil to the electromagnetic field and the acoustical energy may be detected by gauge 100 (block 1508). For example, layered stratified data may be obtained from an IDCP.

In block 1510, an error correction matrix may be built using the raw data of the response. The raw data may be corrected using MPC 151 for producing error corrected data in accordance with the processes and techniques described herein (block 1512). Soil property values of interest may be mapped using adaptive signal processing (block 1514). In block 1516, a moisture value, such as moisture content, may be determined. Systematic error correction can also be applied here. This includes the gauge calibration to take manage inaccuracies of the electronic and mechanical components of the gauge.

Next, in block 1518, it is determined whether to calculate modulus or density for the soil. The determination may be made, for example, based on operator selection of modulus or density. If modulus is determined, a moisture correction process as described herein may be applied for determining corrected property values (block 1520). Further, the property values may be displayed and stored (block 1522).

If density is determined in block 1518, an acoustic-to-density mapping routine may be applied (block 1522) and the moisture correction process applied as described herein for determining corrected property values (block 1520). The property values may be displayed and stored (block 1522).

Density may be calculated acoustically or electromagnetically. These values can be used alone or averaged together as they are obtained independently. Modulus can be calculated independently, as the electromagnetic values can yield void ratios which can be implemented in predictive equations.

Figure 16:
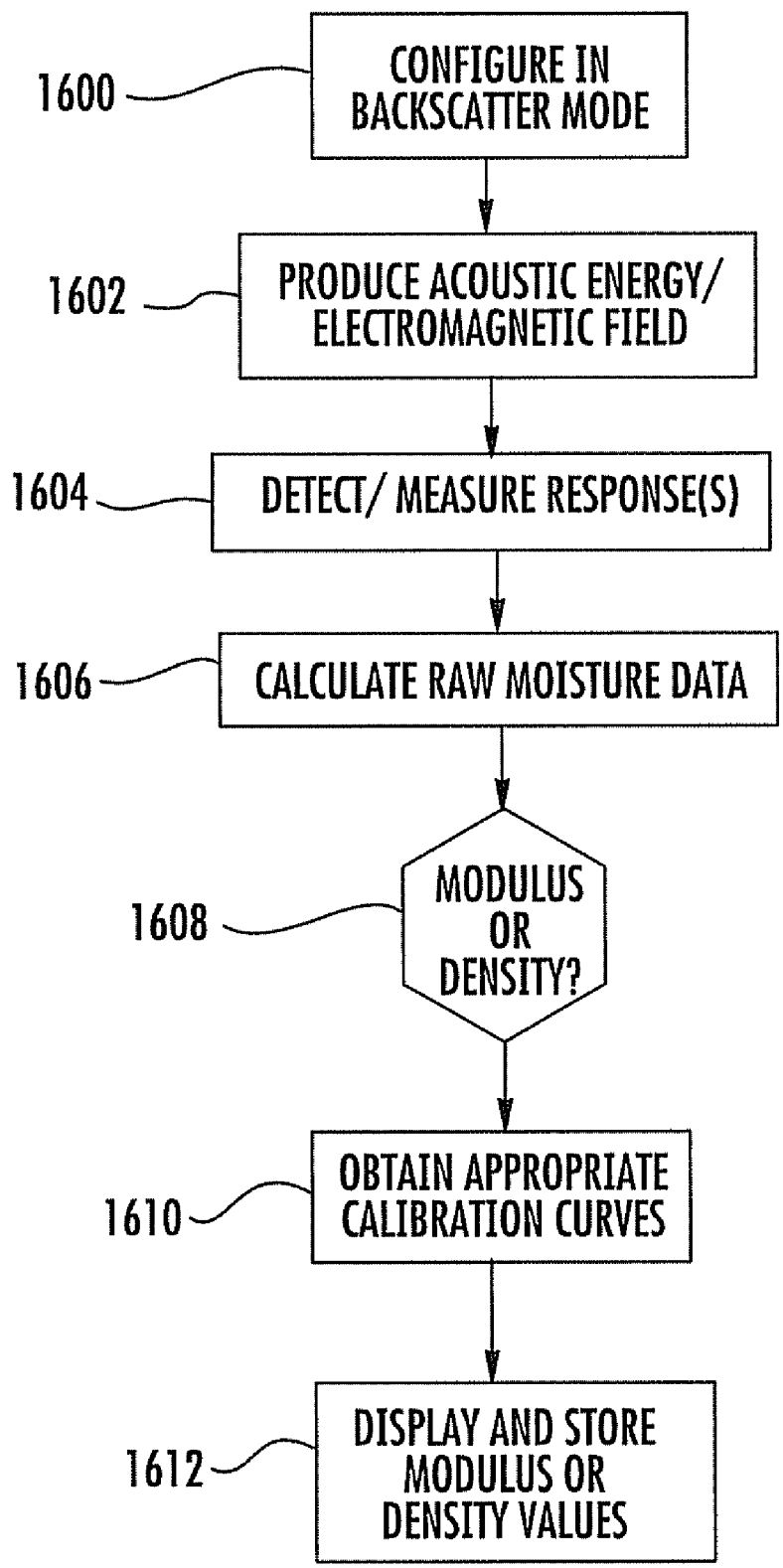
FIG. 16 is a flow chart of an exemplary process for measuring asphalt modulus according to an embodiment of the subject matter described herein.

FIG. 16 is a flow chart illustrating an exemplary process for measuring asphalt modulus according to an embodiment of the subject matter described herein. Gauge 100 shown in FIGS. 1A and 2A is referenced in this exemplary process. Referring to FIG. 16, in block 1600, the operator may configure gauge 100 in a backscatter mode as shown in FIG. 2A. In block 1602, gauge 100 may produce an electromagnetic field and acoustical energy into the asphalt. The response of the asphalt to the electromagnetic field and the acoustical energy may be detected by gauge 100 (block 1604). Further, in block 1606, raw moisture data is calculated from the response.

Next, in block 1608, it is determined whether to calculate modulus or density for the asphalt. The determination may be made, for example, based on operator selection of modulus or density. Appropriate calibration curves may be obtained (block 1610). Next, the calibration curves, response data, and moisture data may be used for calculating modulus or density. The modulus or density values may be displayed and stored (block 1612).

Figure 17:
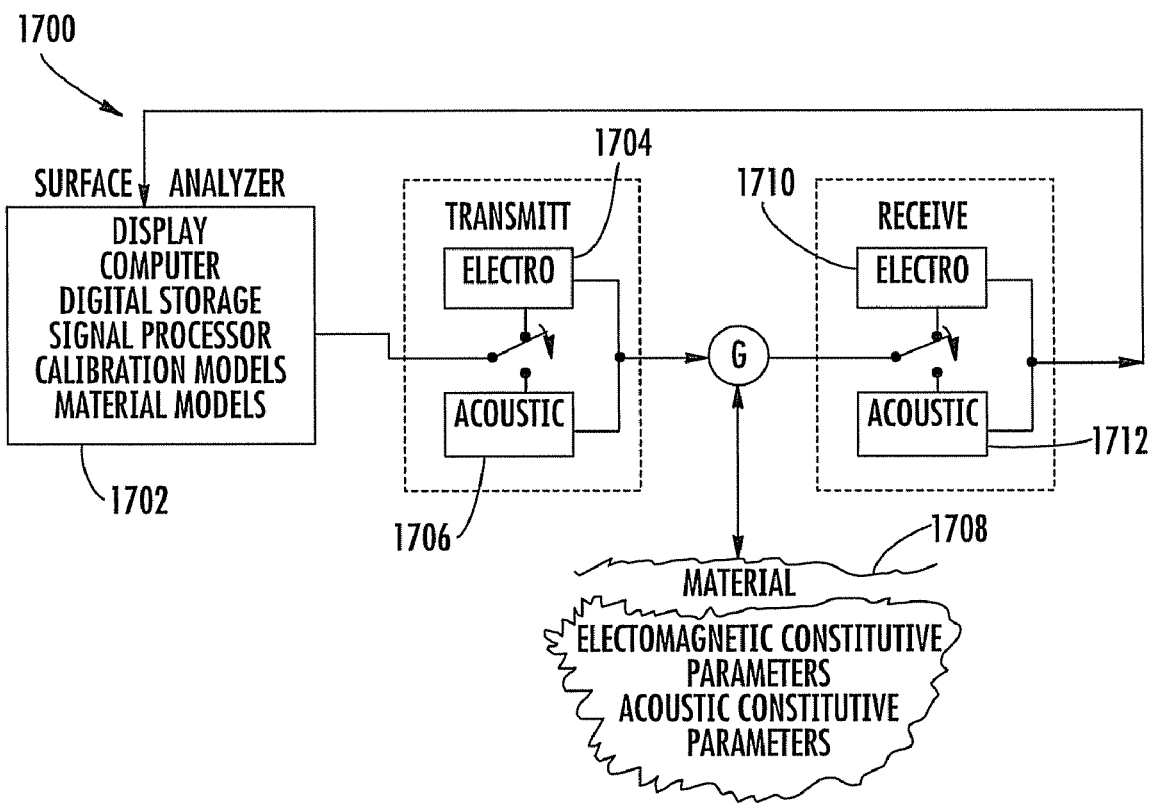
FIG. 17 is a block diagram showing operation of a material property gauge according to an embodiment of the subject matter described herein.

FIG. 17 is a block diagram illustrating operation of a material property gauge 1700 according to an embodiment of the subject matter described herein. Referring to FIG. 17, gauge 1700 includes a display, computer system, digital storage, signal processing equipment, calibration models, and material models, as represented by block 1702. During operation, gauge 1700 may switch between either one of an electromagnetic mode 1704 and an acoustic mode 1706 electromagnetic or acoustic measurements, respectively, as described herein. In electromagnetic generation mode 1704, gauge 1700 may apply an electromagnetic field to a construction material 1708. When in electromagnetic generation mode 1704, gauge 1700 may also function in an electromagnetic receive mode 1710 for receiving response by material 1708. In acoustic generation mode 1706, gauge 1700 may apply acoustic energy to construction material 1708. When in acoustic generation mode 1706, gauge 1700 may also function in an acoustic receive mode 1712 for receiving response by material 1708. The responses can include electromagnetic and acoustic constitutive parameters of material 1708. The response data can be used for calculating property values of material 1708 according to the subject matter described herein.

Figure 18:
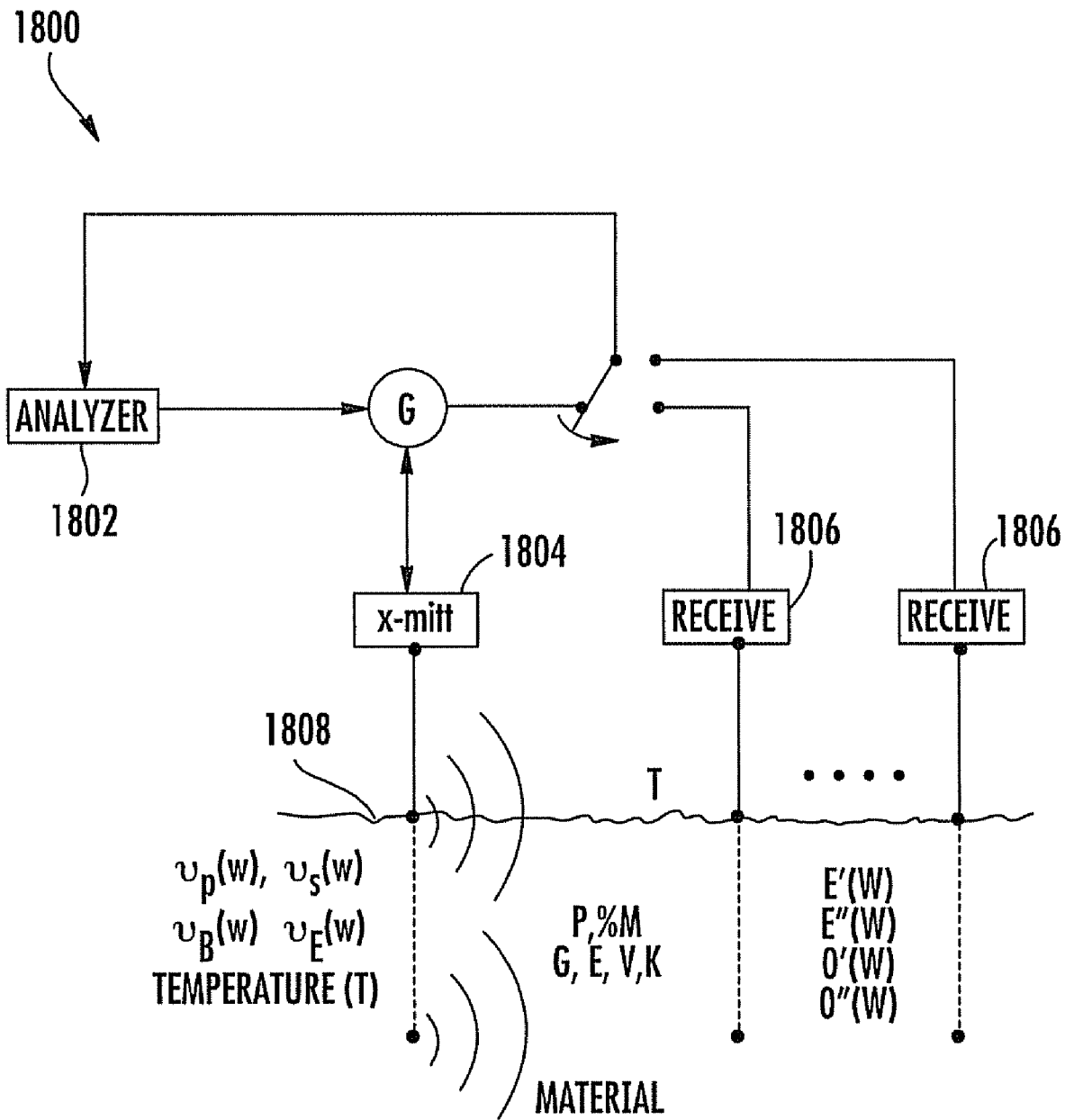
FIG. 18 is a block diagram showing operation of a material property gauge according to an embodiment of the subject matter described herein.

FIG. 18 is a block diagram illustrating operation of a material property gauge 1800 according to an embodiment of the subject matter described herein. Referring to FIG. 18, gauge 1800 includes a display, computer system, digital storage, signal processing equipment, calibration models, and material models, as represented by block 1802. During operation, gauge 1800 may switch between either one of a self-impedance (or reflection-type) mode and a transmission type measurement mode, as described herein. Gauge 1800 may include a transmitter 1804 and one or more receivers 1806. The transmission may transmit electromagnetic or acoustic energy into a construction material 1808. Receivers 1806 may receive a response by material 1808 to the transmitted electromagnetic or acoustic energy. Further, gauge may be configured for transmission in a backscatter mode and/or transmission mode as described herein. The responses may be used by gauge 1800 for calculating property values of material 1808 according to the subject matter described herein.

Figure 19:
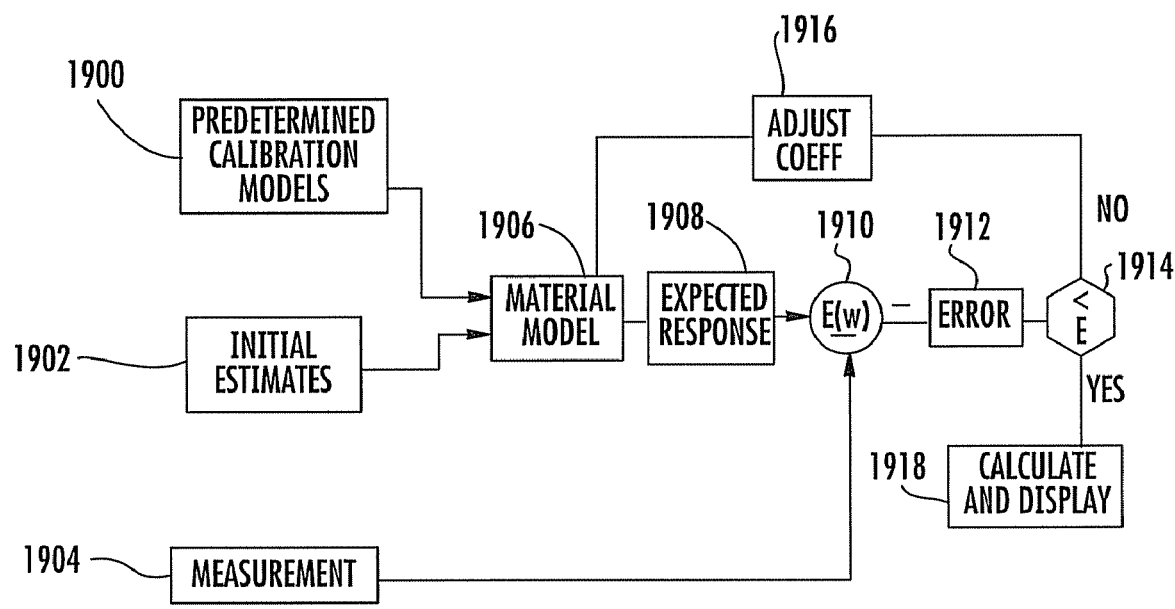
FIG. 19 is a flow chart illustrating an exemplary process for calculating a property value of a construction material according to an embodiment of the subject matter described herein.

FIG. 19 is a flow chart illustrating an exemplary process for calculating a property value of a construction material according to an embodiment of the subject matter described herein. Referring to FIG. 19, an MPC in a material property gauge according to the subject matter described herein may receive one or more predetermined calibration models (block 1900), initial estimates (block 1902), and material property measured responses by a construction material to electromagnetic fields and/or acoustic energy (block 1904). The initial estimates may include one or more of the following root finders and predetermined calibration curves.

In block 1906, the predetermined calibration models and measured responses may be applied to a material model. An expected response based on the inputs and material model may be determined at block 1908. The expected response may include an expected curve, which is a function of the multiple parameters and the construction material's response to input electromagnetic fields and/or acoustic energy.

In block 1910, the expected response determined in block 1908 is compared to the measured response of block 1904. Based on the comparison, an error may be generated at block 1912. Next, in block 1914, it is determined whether the error is less than a predetermined error value. If the error is not less than the predetermined error value, coefficients are adjusted (block 1916) and the process returns to block 1906. Otherwise, property values for the construction material are calculated and displayed (block 1918).

Material property gauges according to the subject matter described herein may be operable in several different modes of operation for obtaining measurements for use in calculating property values of sample or construction materials. For example, the gauge may be configured for measuring acoustic energies in either a down hole or uphole configuration. In the down hole configuration, a penetrometer of the gauge may be positioned in a transmission mode. In an uphole configuration, a penetrometer of the gauge may be positioned in a backscatter mode. Further, a gauge may be positioned in a down hole mode for obtaining dielectric measurements of water, dispersion measurements for soil density, and classification-related information. Further, a gauge may be positioned in a backscatter mode for using an electromagnetic generator/source for obtaining electromagnetic field measurements for asphalt density calculations. Further, a gauge may be positioned in a backscatter mode for using an acoustic source for obtaining acoustic energy measurements for modulus and soil density calculations. Further, in one embodiment, a combination of acoustic measurements, dispersive measurements, and electromagnetic dispersion measurements may be used for calculations of density, modulus, and correction data based on moisture and temperature measurements.

It will be understood that various details of the subject matter described herein may be changed without departing from the scope of the subject matter described herein. Furthermore, the foregoing description is for the purpose of illustration only, and not for the purpose of limitation, as the subject matter described herein is defined by the claims as set forth hereinafter.

What is claimed is:

1. A material property gauge for determining a property of construction material, the material property gauge comprising:
   an electromagnetic field generator configured to generate an electromagnetic field including two or more frequencies between a radio frequency (RF) range and a microwave frequency range and for penetrating into a hydrated, heterogeneous construction material;
   an electromagnetic sensor operable to measure a response of the construction material to the electromagnetic field and operable to produce a signal representing the measured electromagnetic response by the construction material to the electromagnetic field;
   a calibration function configured to obtain a calibration curve for the construction material based on one or more of a moisture content, a density, and a modulus of the construction material; and
   a material property calculation function configured to calculate a material property value associated with the construction material based upon the signal produced by the electromagnetic sensor, wherein calculating the material property value includes using the electromagnetic response to determine a moisture content and a density of the construction material.

2. The material property gauge of claim 1 wherein the electromagnetic sensor comprises a device selected from the group consisting of a fringing field sensor, an electromagnetic nearfield sensor, an electromagnetic farfield sensor, a microwave resonator, and an antenna.

3. The material property gauge of claim 1 wherein the construction material comprises a material selected from the group consisting of soil, asphalt, pavement, stone, sub-base material, concrete, and sub-grade material.

4. The material property gauge of claim 1 wherein the electromagnetic field generator comprises a device selected from the group consisting of a voltage controlled oscillator (VCO), a Clapp oscillator, a relaxation oscillator, a ring oscillator, an RC oscillator, a crystal oscillator, a blocking oscillator, a phase-locked oscillator, a voltage oscillator, a multivibrator, a Gunn diode, a numerically-controlled oscillator, a Kystron tube, a high-power microwave magnetron, a backward wave oscillator, a VLF transmitter, an integrated circuit timer, an arbitrary waveform generator, a pulse-width modulation device, an analog synthesizer, current sources, synthesized sources, YIG-tuned oscillators, and integrated circuits.

5. The material property gauge of claim 1 wherein the material property calculation function is configured to correct a density calculation of the construction material based on the signal produced by the electromagnetic sensor.

6. The material property gauge of claim 5 wherein the signal produced by the electromagnetic sensor represents a moisture property value associated with the construction material.

7. The material property gauge of claim 1 wherein the signal produced by the electromagnetic sensor represents a voids value associated with the construction material.

8. A method for determining a property of construction material, the method comprising:
   generating an electromagnetic field including two or more frequencies between a radio frequency (RF) range and a microwave frequency range and penetrating into a hydrated, heterogeneous construction material;
   measuring a response of the construction material to the electromagnetic field;
   producing a signal representing the measured response by the construction material to the electromagnetic field;

obtaining a calibration curve for the construction material based on one or more of a moisture content, a density, and a modulus of the construction material; and calculating a material property value associated with the construction material based upon the produced signal, wherein calculating the material property value includes using the measured electromagnetic response to determine a moisture content and a density of the construction material.

9. The method of claim 8 wherein the construction material comprises a material selected from the group consisting of soil, asphalt, pavement, stone, sub-base material, concrete, and sub-grade material.

10. The method of claim 8 comprising correcting a density calculation of the construction material based on the signal produced by the electromagnetic sensor.

11. The method of claim 8 comprising correcting a density calculation of the construction material based on the signal representing the measured response by the construction material to the electromagnetic field.

12. The method of claim 8 comprising displaying the calculated property value.

13. A computer program product comprising computer executable instruction embodied in a computer readable medium for performing steps comprising:

generating an electromagnetic field including two or more frequencies between a radio frequency (RF) range and a microwave frequency range and penetrating into a hydrated, heterogeneous construction material;

measuring a response of the construction material to the electromagnetic field;

producing a signal representing the measured response by the construction material to the electromagnetic field;

obtaining a calibration curve for the construction material based on one or more of a moisture content, a density, and a modulus of the construction material; and calculating a material property value associated with the construction material based upon the produced signal, wherein calculating the material property value includes using the measured electromagnetic response to determine a moisture content and a density of the construction material.

14. The computer program product of claim 13 wherein the construction material comprises a material selected from the group consisting of soil, asphalt, pavement, stone, sub-base material, sub-grade material, cement.

15. The computer program product of claim 13 comprising correcting a density calculation of the construction material based on the signal produced by the electromagnetic sensor.

16. The computer program product of claim 13 comprising correcting a density calculation of the construction material based on the signal representing the measured response by the construction material to the electromagnetic field.

17. The computer program product of claim 13 comprising displaying the calculated property value.

18. The material property gauge of claim 1 wherein material property calculation function configured to calculate a density-independent moisture content of the construction material.

19. The method of claim 8 comprising calculating a density-independent moisture content of the construction material.

20. The material property gauge of claim 1 comprising a temperature sensor operable to measure a temperature associated with the construction material and operable to produce a signal representing the measured temperature associated with the construction material.

21. The material property gauge of claim 20 wherein the temperature sensor comprises a device selected from the group consisting of an infrared heat sensor, an optical infrared sensor, a resistance temperature detector (RTD), a thermocouple, a solid state-based temperature sensor, and a resistive-based temperature sensor.

22. The method of claim 8 comprising detecting a response of the construction material to temperature and producing a signal representing the detected response by the construction material to the temperature.

23. The material property gauge of claim 20 wherein the material property calculation function is configured to calculate a density of the construction material based on the signals produced by the electromagnetic sensor and the temperature sensor.

24. The material property gauge of claim 20 wherein the material property calculation function is configured to correct a density calculation of the construction material based on the signal produced by the temperature sensor.

25. The material property gauge of claim 20 wherein the material property calculation function is configured to calculate one or more of a density, a moisture value, and a modulus of the construction material based on the signals produced by the electromagnetic sensor and the temperature sensor.

26. The material property gauge of claim 20 comprising a display operable to display the property value associated with the electromagnetic sensor and the temperature sensor.

\* \* \* \* \*